(12) United States Patent
Gharib et al.

(10) Patent No.: US 7,524,298 B2
(45) Date of Patent: *Apr. 28, 2009

(54) DEVICE AND METHOD FOR TREATING HYDROCEPHALUS

(75) Inventors: Morteza Gharib, San Marino, CA (US); Derek Rinderknecht, Pasadena, CA (US); Mostafa Gharib, Cologne (DE)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/137,852

(22) Filed: May 24, 2005

(65) Prior Publication Data

US 2005/0277865 A1 Dec. 15, 2005

Related U.S. Application Data

(60) Provisional application No. 60/574,431, filed on May 25, 2004.

(51) Int. Cl.
*A61M 1/36* (2006.01)
*F04B 4/38* (2006.01)

(52) U.S. Cl. .......................... 604/9; 417/474

(58) Field of Classification Search ............... 604/7–10, 604/6.11, 151; 606/153; 623/3.1, 3.16, 3.17; 417/53, 474
See application file for complete search history.

(56) References Cited

U.S. PATENT DOCUMENTS

| | | | |
|---|---|---|---|
| 3,756,243 A | 9/1973 | Schulte | |
| 4,240,434 A * | 12/1980 | Newkirk | 604/9 |
| 4,657,530 A * | 4/1987 | Buchwald et al. | 604/9 |
| 4,681,559 A * | 7/1987 | Hooven | 604/9 |
| 4,867,740 A * | 9/1989 | East | 604/9 |
| 4,883,456 A * | 11/1989 | Holter | 604/9 |
| 5,372,573 A * | 12/1994 | Habib | 600/16 |
| 5,599,638 A | 2/1997 | Surampudi et al. | |
| 5,637,083 A | 6/1997 | Bertrand et al. | |
| 5,773,162 A | 6/1998 | Surampudi et al. | |
| 5,795,496 A | 8/1998 | Yen et al. | |
| 6,136,463 A | 10/2000 | Kindler et al. | |
| 6,150,047 A | 11/2000 | Yen et al. | |
| 6,171,721 B1 | 1/2001 | Narayanan et al. | |
| 6,221,523 B1 | 4/2001 | Chun et al. | |
| 6,254,355 B1 * | 7/2001 | Gharib | 417/53 |
| 6,254,748 B1 | 7/2001 | Surampudi et al. | |
| 6,264,625 B1 | 7/2001 | Rubenstein et al. | |
| 6,265,093 B1 | 7/2001 | Surampudi et al. | |
| 6,277,447 B1 | 8/2001 | Chun et al. | |
| 6,299,744 B1 | 10/2001 | Narayanan et al. | |
| 6,303,244 B1 | 10/2001 | Surampudi et al. | |
| 6,306,285 B1 | 10/2001 | Narayanan et al. | |
| 6,368,492 B1 | 4/2002 | Narayanan et al. | |
| 6,391,486 B1 | 5/2002 | Narayanan et al. | |
| 6,399,235 B1 | 6/2002 | Yen et al. | |

(Continued)

*Primary Examiner*—Leslie R Deak
(74) *Attorney, Agent, or Firm*—Law Ofc Scott C Harris

(57) ABSTRACT

A shunt system for use in a human body that is formed from a length of tube that is configured as a pump. The length of tube may be configured as a hydroimpedance pomp, whose surfaces are pressed to pump fluid in the specified direction and way. The length of tube that forms the pump may be connected to shunt inlet and outlet parts, and may also include a valve that is adjustable to prevent back draining of fluid.

15 Claims, 19 Drawing Sheets

U.S. PATENT DOCUMENTS

| | | |
|---|---|---|
| 6,420,059 B1 | 7/2002 | Surampudi et al. |
| 6,432,284 B1 | 8/2002 | Narayanan et al. |
| 6,440,594 B1 | 8/2002 | Kindler et al. |
| 6,444,341 B1 | 9/2002 | Yen et al. |
| 6,468,684 B1 | 10/2002 | Chisholm et al. |
| 6,533,919 B1 | 3/2003 | Narayanan et al. |
| 6,589,684 B1 | 7/2003 | Surampudi et al. |
| 6,680,139 B2 | 1/2004 | Narayanan et al. |
| 6,703,150 B2 | 3/2004 | Surampudi et al. |
| 6,740,434 B2 | 5/2004 | Surampudi et al. |
| 6,756,145 B2 | 6/2004 | Narayanan et al. |
| 6,821,659 B2 | 11/2004 | Surampudi et al. |
| 2001/0052389 A1 | 12/2001 | Chun et al. |
| 2002/0058178 A1 | 5/2002 | Narayanan et al. |
| 2003/0008190 A1 | 1/2003 | Chisholm et al. |
| 2003/0226763 A1 | 12/2003 | Narayanan et al. |
| 2004/0166397 A1 | 8/2004 | Valdez et al. |
| 2004/0229108 A1 | 11/2004 | Valdez et al. |
| 2004/0234834 A1 | 11/2004 | Narayanan et al. |
| 2005/0003254 A1 | 1/2005 | Surampudi et al. |
| 2005/0042487 A1 | 2/2005 | Surampudi et al. |
| 2005/0221142 A1 | 10/2005 | Narayanan et al. |

* cited by examiner

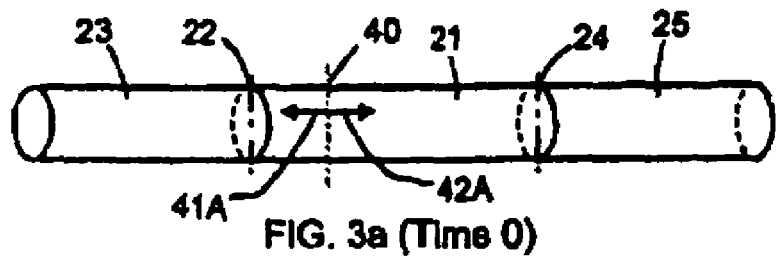
FIG. 3a (Time 0)
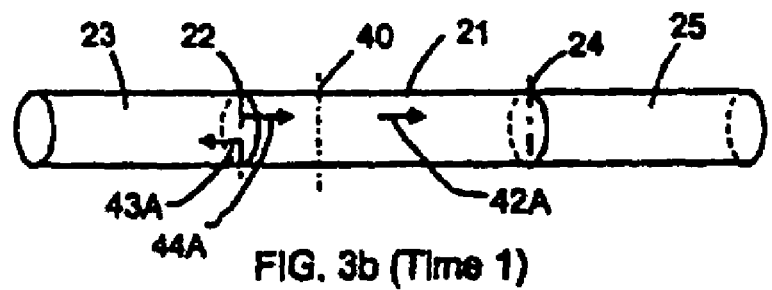
FIG. 3b (Time 1)
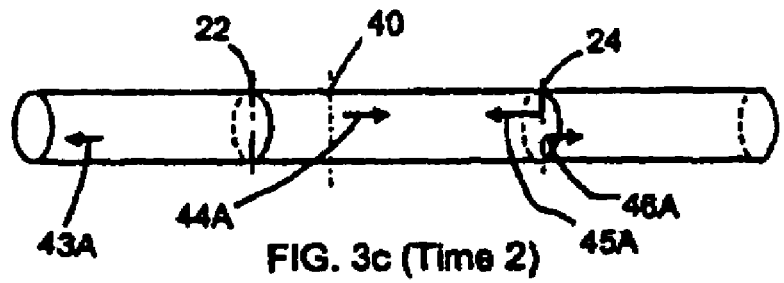
FIG. 3c (Time 2)
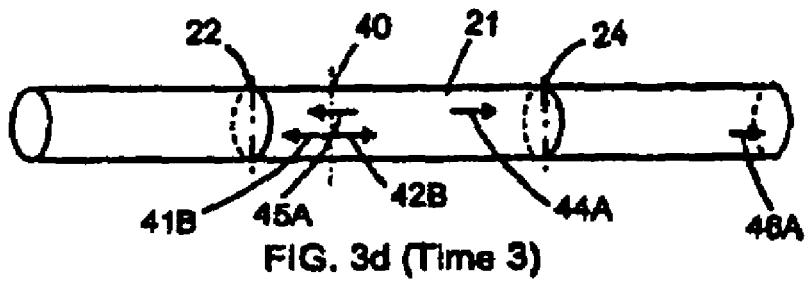
FIG. 3d (Time 3)
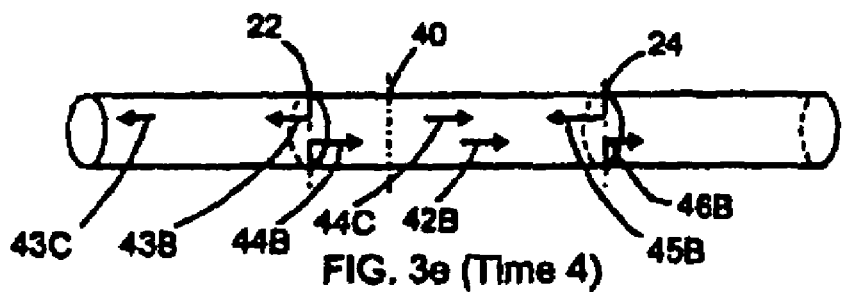
FIG. 3e (Time 4)
FIG. 3

DEVICE AND METHOD FOR TREATING HYDROCEPHALUS

CROSS-REFERENCE TO RELATED APPLICATION

The present application claims priority to provisional application 60/574,431 filed May 25, 2004, the entire contents of which are incorporated herein by reference.

FIELD

This application describes an active catheter shunt system and methods for pumping fluid. More particularly, the application relates to a catheter shunt having a valveless hydroimpedance pumping system for draining excess cerebrospinal fluid and relieving symptoms of hydrocephalus.

BACKGROUND

Passive shunting systems are often subject to functional failures such as over drainage, under drainage or blockage. These can prevent effective treatment and may cause the symptoms of disease to recur. Such shunting systems operate based on physiological pressure gradients and therefore must rely on increasing the shunt diameter to decrease the flow resistance, in order to provide increased flow. Increases in inner diameter however make shunting systems quite bulky. This can make the device less convenient and can lead to patient discomfort.

Issues for an active catheter shunt system may include the method by which fluid is pumped, and miniaturization of the pumping device.

Current miniaturized pumping concepts often operate at high pressures, which can be damaging to the surrounding tissues. A tubular hydroimpedance pump is particularly well suited for applications in biomedicine because it can operate bidirectionally under low pressure, high flow conditions. Examples of such applications include venous valve prosthesis for chronic venous insufficiency, esophageal sphincter valve prosthesis for gastroesophageal reflux disease, shunting prosthesis for hydrocephalus, aqueous drainage shunt for glaucoma, portacaval shunt for treating high blood pressure in the liver, ventriculoperitoneal shunt to relieve cerebrospinal fluid, endolymphatic shunt to relieve the symptoms of vertigo and hearing loss due to endolymphatic hydrops, Blalock-Taussig shunt for aorta-to-the pulmonary artery bypass, and others.

Many different systems available for pumping fluid. These systems commonly use impellers, a set of blades, gears, or pistons in order to transfer the energy to drive the fluid in a specific direction. These systems however involve moving parts which are subject to wear due to friction, ultimately limiting the lifetime of the device. Less conventional pump designs such as peristaltic pumps, or diaphragm pumps are also known. These pumps however rely on the displacement of relatively large surface areas. In a regime where viscous forces are dominant, large machinery is often required to produce the pressure necessary to drive the fluid rendering these concepts unsuitable for applications where the fluid can be damaged or space is limited. In addition, special features to prevent hemolysis are not usually available in the current pump designs.

U.S. Pat. Appl. publication No. 2003/0185692 to Ng et al, discloses a valveless micropump comprising: a hollow pump chamber having a driving element coupled thereto; an inlet channel coupled to the hollow pump chamber; an outlet channel coupled to the hollow pump chamber; the inlet channel, the hollow pump chamber and the outlet channel defining a fluid Flow path through the inlet channel, the hollow pump chamber, and the outlet channel; and at least one direction-sensitive element disposed in the flow path within one of the inlet and outlet chambers, wherein the at least one direction-sensitive element comprises an airfoil.

U.S. Pat. No. 6,254,355 to Morteza Gharib, one of co-inventors of the present invention, the entire contents of which are incorporated herein by reference, discloses a valveless fluid system based on pinch-off actuation of an elastic tube channel at a location situated asymmetrically with respect to its two ends. Means of pinch-off actuation can be either electromagnetic, pneumatic, mechanical, or the like. The hydro-elastic pump therein must have the elastic tube attached to other segments that have a different compliance (such as elasticity). This difference in the elastic properties facilitates elastic wave reflection in terms of local or global dynamic change of the tube's cross-section. This results in the establishment of a pressure difference across the pump and thus unidirectional movement of fluid. The intensity and direction of this flow depends on the frequency, duty cycle, and elastic properties of the tube.

In a copending application U.S. patent application Ser. No. 10/382,721, filed Mar. 4, 2003, a method for pumping fluid is disclosed, comprising: pinching a portion of an elastic element in a way which increases a pressure in a first end member of the elastic element more than a pressure in a second end member of the elastic element without valve action, to cause a pressure differential, wherein the end members have different hydroimpedance; and using the pressure differential to move fluid between the first and second end members. The pinching mechanism is carried out by a device mounted on the exterior surface of the elastic element, which is obstructive in applications.

The elastic wave reflection of a hydro-elastic pump depends on the hydroimpedance of the segments. In the prior art hydro-elastic pump, it was required that the segments to be stiffer either by using a different material or using reinforcement. To overcome the limiting conditions of the prior hydro-elastic pump systems, it is disclosed herein that the pinching location separates two segments with different hydroimpedances, including but not restricted to the characteristic impedance or any impedance in which attenuation occurs over distance, with certain frequency and duty cycle to form asymmetric forces that pump fluid achieving a non-rotary bladeless and valveless pumping operation.

SUMMARY

Some aspects relate to a method for draining body fluid, comprising: providing a shunt system comprising a collector tube having a tip section, a discharge tube having an end section, and pump that interconnects the collector tube and the discharge tube; implanting the shunt system in a patient, wherein the tip section is disposed in a region of the human body to be drained and the end section is disposed in a region into which the fluid is to be discharged; and initiating pumping action of the pump.

Some aspects relate to a method for treating hydrocephalus, comprising: providing a catheter shunt system comprising a collector catheter having a tip section, a discharge catheter having an end section, and a pump that interconnects the collector catheter and the discharge catheter; implanting the shunt system in a patient, wherein the tip section is disposed in brain ventricles of the patient and the end section is disposed in a body cavity of peritoneal cavity or an atrium; and initiating pumping action of the pump. This pump may be but is not limited to one of the following: gear, impeller, peristaltic, diaphragm, screw, magnetic flux, or hydroimpedance.

Some aspects relate to a catheter shunt system comprising a collector catheter, a discharge catheter, and a hydroimpedance pump, wherein the hydroimpedance pump interconnects the collector catheter and the discharge catheter.

An aspect describes a valveless pump comprised of an elastic element having divided into two segments by the location of a pinching actuator, the first segment comprising the elastic element from the pinching location to the first end and all of its subsequent attachments and a second end segment comprising the elastic element from the pinching location to the second end and all its subsequent attachments, wherein the first segment has a hydroimpedance different from the hydroimpedance of the second segment. In one preferred embodiment, the pump further comprises pressure change means for inducing a pressure increase and a pressure decrease into the first and second segments, in a way which causes a pressure difference between the first and second segments, resulting in flow.

Another aspect describes a method for pumping fluid comprising changing a shape of or pinching an elastic element in a way which increases a pressure in a first end segment of the elastic element more than a pressure in a second end segment of the elastic element without valve action, to cause a pressure differential, wherein the segments have different impedance, and using the pressure differential to move fluid between the first and second segments.

Another aspect describes a valveless pump comprising an elastic element having a length with a first flexible wall segment and a spaced apart second flexible wall segment, and a first external chamber mounted over the first flexible wall segment and a second external chamber mounted over the second flexible wall segment, wherein a pressure is applied through the first external chamber onto the first flexible wall segment that is different from a pressure applied onto the second flexible wall segment. In one embodiment, the pump further comprises pressure change means for inducing a pressure increase and a pressure decrease into the first and second flexible wall segments, in a way which causes a pressure difference between the first and second segments, and causes a pumping action based on the pressure difference.

BRIEF DESCRIPTION OF THE DRAWINGS

Further features and advantages of the present invention will become apparent to one of skill in the art in view of the Detailed Description that follows, when considered together with the attached drawings and claims.

FIG. 3a-3e shows mechanisms of a basic hydroimpedance pump for inducing flow direction at a sequence of time following the pinch-off initiation.

DETAILED DESCRIPTION

Figure 1:
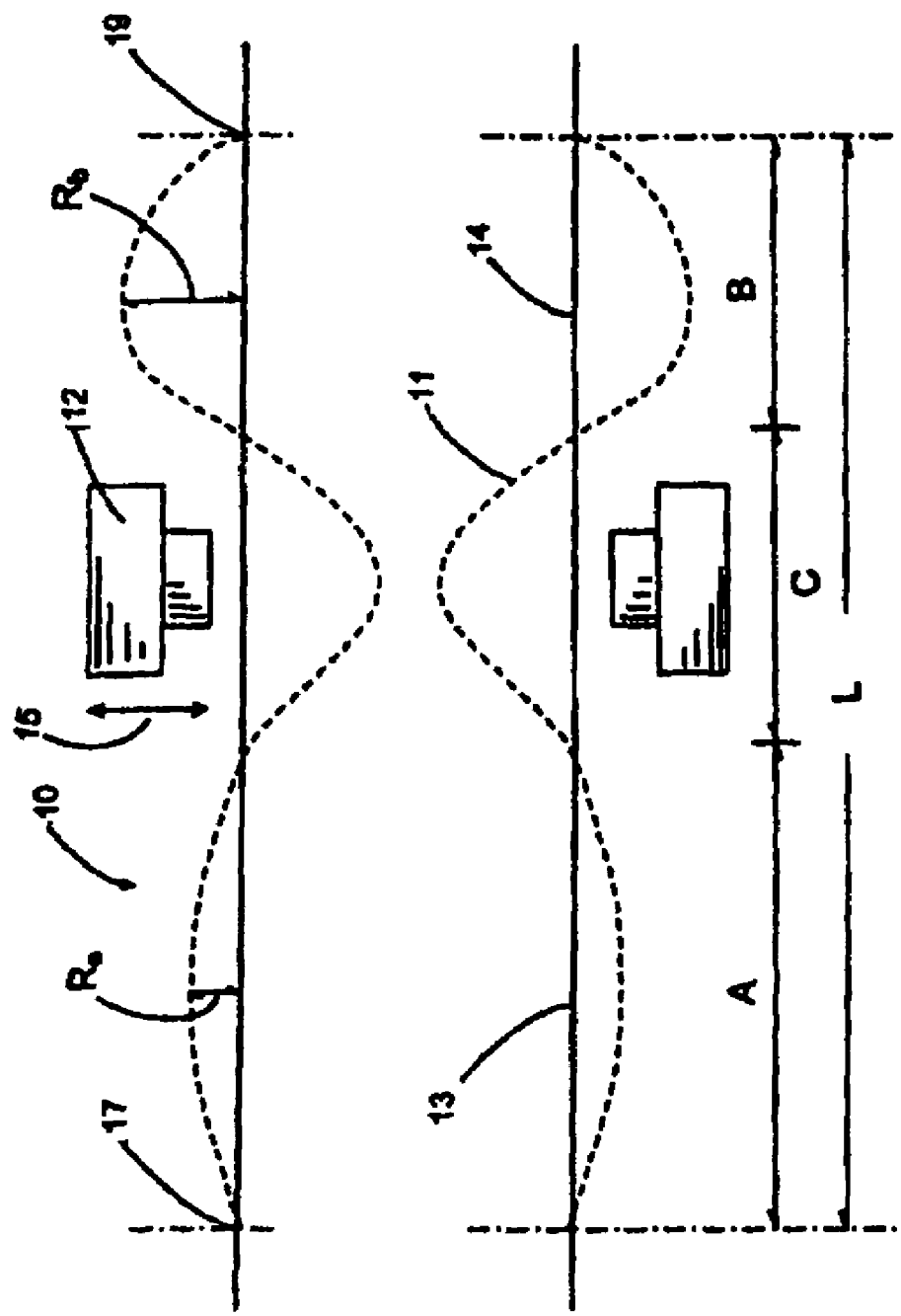
FIG. 1 is a hydroelastic pump of the prior art for illustration.

The tubular hydroimpedance pump is useful and applicable in medical and biomedical applications, such as venous valve prosthesis for chronic venous insufficiency, esophageal sphincter valve prosthesis for gastroesophageal reflux disease, shunting prosthesis for hydrocephalus, aqueous drainage shunt for glaucoma, portacaval shunt for treating high blood pressure in the liver, ventriculoperitoneal shunt to relieve cerebrospinal fluid, endolymphatic shunt to relieve the symptoms of vertigo and hearing loss due to endolymphatic hydrops, Blalock-Taussig shunt for aorta-to-the pulmonary artery bypass, and any other application that requires pumping for medical purposes.

When the flow of cerebrospinal fluid (CSF) is normal and unobstructed, new CSF is constantly produced, flowing into the ventricles and out of the brain again. Hydrocephalus can occur for one of two basic reasons: when there is an obstruction in one of the CSF pathways, or CSF is not being permitted to be reabsorbed. When a shunt is implanted in a person with hydrocephalus, a goal is for the shunt system to mimic what would occur in the body naturally. CSF is drained by the shunt, and the flow is regulated so that a constant intracranial pressure (ICP) is maintained within the brain.

In one aspect, a method for treating hydrocephalus uses a catheter shunt system that has a collector catheter having a tip section, a discharge catheter having an end section, and an hydroimpedance pump that interconnects the collector catheter and the discharge catheter; implanting the shunt system in a patient, wherein the tip section is disposed in brain ventricles of the patient and the end section is disposed in a body cavity of peritoneal cavity or an atrium; and initiating pumping action of the hydroimpedance pump.

The principle of a shunt include causing the CSF to enter the shunt system through small openings, e.g., holes or slits near the tip of the proximal catheter. As CSF is produced by the choroid plexus, the shunt valve regulates the amount of ICP by draining fluid from the ventricles. CSF flows from the proximal catheter through the valve system and into the distal catheter, which drains CSF into another area of the body where it can be reabsorbed (directly or indirectly) by the bloodstream. In another embodiment, CSF flows out of the distal catheter into the peritoneal cavity. This typically causes the body no harm, because CSF is normally reabsorbed by the superior sagittal sinus; a large venous structure that carries the blood flow away from the brain.

Most shunt valves are differential pressure valves. This means that the valves are self-regulating, capable of gauging the amount of ICP, and can adjust to differential pressures between the ventricles and the distal cavity the shunt drains into. This allows the right amount of CSF to be drained based on ICP. The most common pressure ratings for differential pressure valves are: Extra-low-pressure: 0-10 mm $H_2O$; Low-pressure: 10-50 mm $H_2O$; Medium-pressure: 51-100 mm $H_2O$; and High-pressure: 101-200 mm $H_2O$. The values listed above are based on information supplied from various shunt manufacturers. The amount of fluid that is allowed to flow through the shunt valve depends on the specific design characteristics of the valve, as well as levels that are rated by the manufacturer of the shunt valve. The flow of CSF through the valve can be changed by the pressure of tissue or debris in the shunt system.

Unidirectional valves in CSF shunting were used by E. Pay-r in Greifswald in 1908 who implanted formalin-fixed calf veins with preserved venous flaps as ventriculo-sinus sagittalis shunts. Artificial CSF valves were proposed and developed later, for example, a magnetic hold valve, a ball-in-cone valve, a transverse distal slit Teflon valve, a spring augmented silicone proximal slit valve, a combined slit-and ball-construction valve, a diaphragm valve, a longitudinal distal slit silicone valve, and the like.

About 20% of shunt-patients present headaches, subdurals, cranial deformations, symptomatic slit-ventricle-syndrome and other complications due to overdrainage or underdrainage. The prevention of inadequate drainage was the aim in the development of the "second generation" devices which may be classified as adjustable valves, for example, a variable-resistance-construction valve, a gravitationally controlled valve, and the like.

Figure 16:
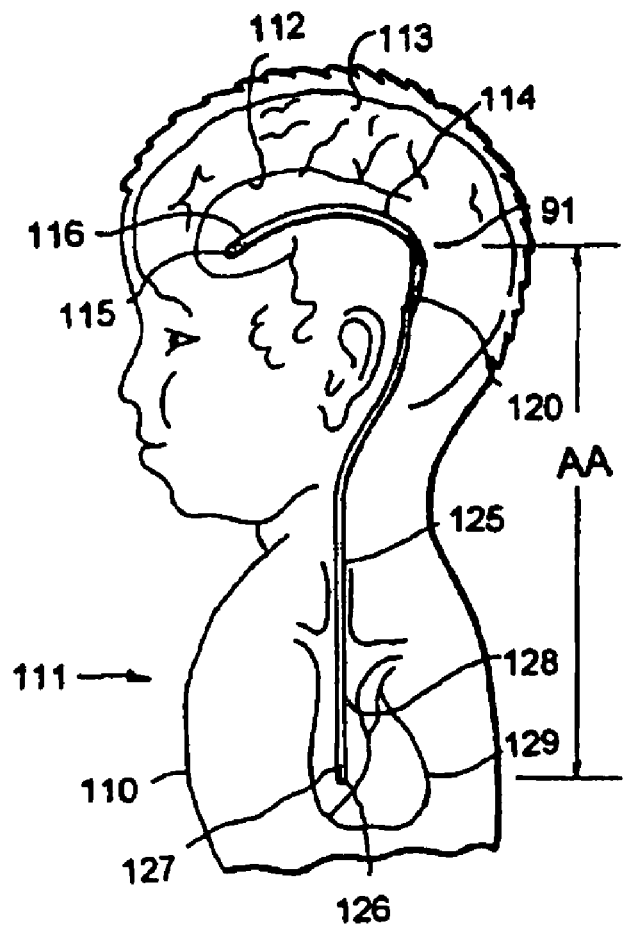
FIG. 16 shows a first side view, partly in schematic notation, showing a catheter shunt system in an upright position of the body.
Figure 17:
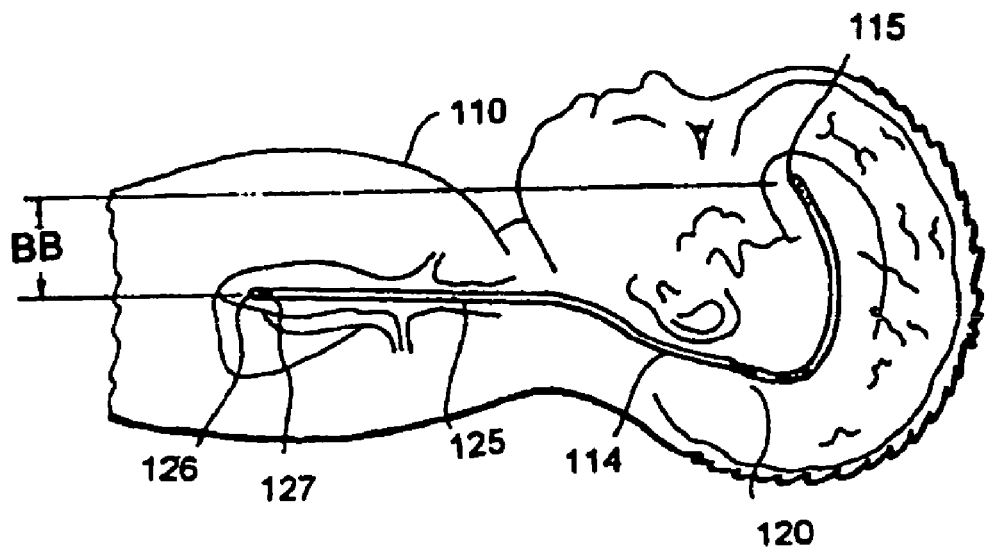
FIG. 17 shows a second side view, partly in schematic notation, showing a catheter shunt system in a supine position of the body.

FIG. 16 shows a first side view, partly in schematic notation, showing a catheter shunt system in an upright position of the body, whereas FIG. 17 shows a second side view showing a catheter shunt system in a supine position of the body. FIG. 16 shows the torso 110 of a human body 111 partially in cutaway and partly in schematic notation. Ventricles 112 of the brain 113 are shown into which a collector catheter 114 of the catheter shunt system 109 is placed for drainage of excessive fluid therefrom. The collector catheter has been passed through an opening drilled in the skull. Its open end 115 is disposed in the ventricles, and its other end is disposed outside the skull. Perforations 116 are provided for flow of liquid into the lumen of the collector catheter. The collector catheter extends downwardly and includes within it an impedance pump 91 of the invention. This pump and other circuit elements generally known in the art can optionally be used along with this invention. In one preferred embodiment, a one-way check valve 20 is provided for unidirectional flow drainage.

The discharge catheter 125 of the catheter shunt system is connected to the outflow end of the pump 91, the lumen of which extends down to a tip 126 with an opening 127. Suitable dispositions of the discharge catheter in the human body are fully described in U.S. Pat. No. 3,111,125. Instead of the tip of the discharge catheter being located in the atrium 128 of the heart 129, it might instead be located in the peritoneal cavity. The ventricles of the brain are sometimes referred to as "a region of the human body to be drained", and the peritoneal cavity or the atrium of the heart is sometimes referred to as "a region into which the fluid is to be discharged".

One-way valve 120 may be useful to prevent fluid from re-flowing into body cavities. First, one may assume for a moment that one-way valve is not present in FIGS. 16 and 17, but instead that the two tubes are connected together without its interposition and with the pump in an open position permitting free flow through the shunt system. In this case, it will be noted that, when the human body is erect as in FIG. 16, there is an elevation AA between the inlet end of the collector catheter 114 and the outlet end of the discharge catheter 125. When the human body is reclining, there is an elevation BB between the catheters which is less than AA. There is, of course, a wide range of possible elevations between these points depending on the position of the human body, and the elevation might even be reduced to zero with the person laying on them with the two tips at substantially the same elevation. The ventricles of the brain, the atrium, and the peritoneal cavity operate at pressures which are relatively close to atmosphere, even though they may be somewhat different from one another. Therefore, changes in position of the body may cause a siphoning action, especially when the person stands up, because the downstream suction exerted in the discharge catheter will be greater in FIG. 16 than in FIG. 17. This is an action which, if permitted to continue, may overdrain the ventricles or such other region which is to be drained, and may, in the case of drainage of the ventricles, lead to headaches and depression of the fontanel. Valve 120 and the shunt system of which it forms a part, may protect against this eventuality. It does so by subjecting the system to closure to flow in the event of undesirably low pressures relative to a reference pressure such as atmospheric.

Figure 18:
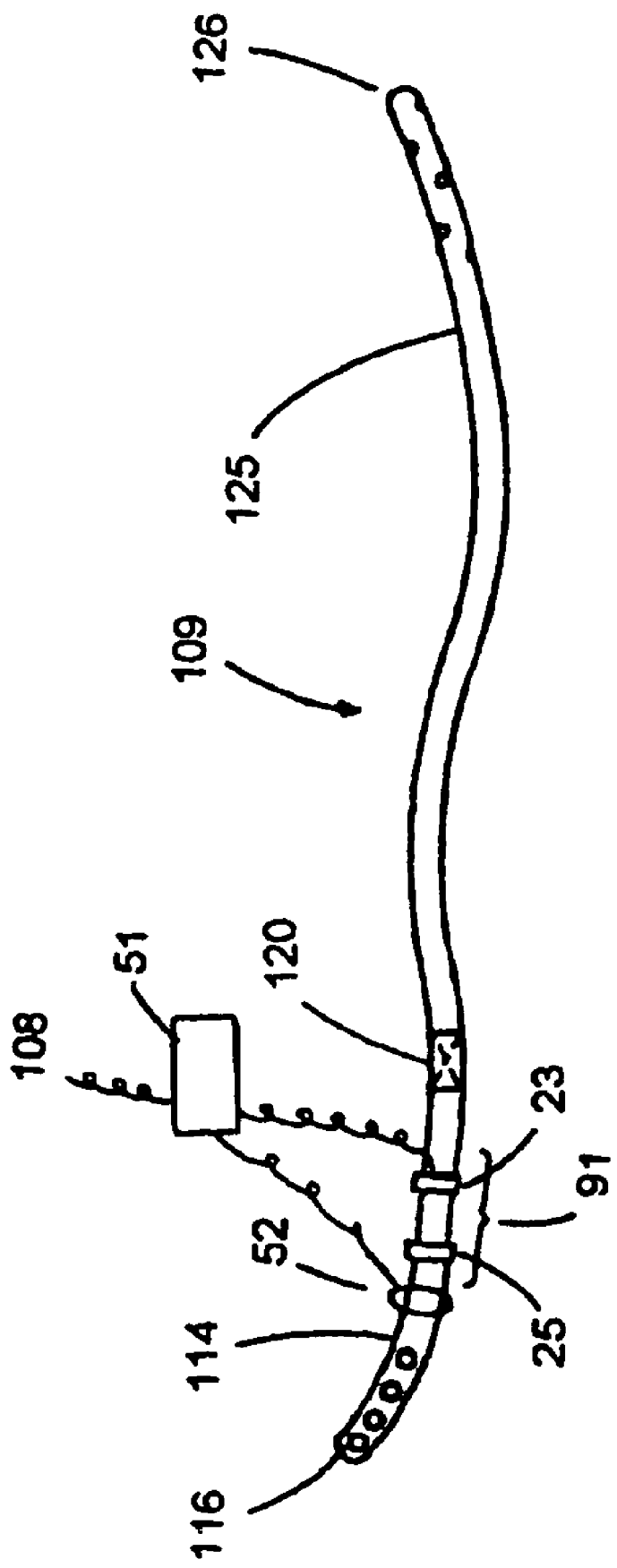
FIG. 18 shows one embodiment of the catheter shunt system according to the principles of the invention.

FIG. 18 shows a catheter shunt system 109 equipped with an impedance pump 91 having a feedback mechanism 51, wherein the inflow end of the impedance pump is connected to a collector catheter 114 and the outflow end is connected to a discharge catheter 125. The pump 91 may further comprise two end members 23, 25 with different impedances. As shown, the sets of coils wounded around the end members are powered from an external energy source 108 or batteries.

Figure 19:
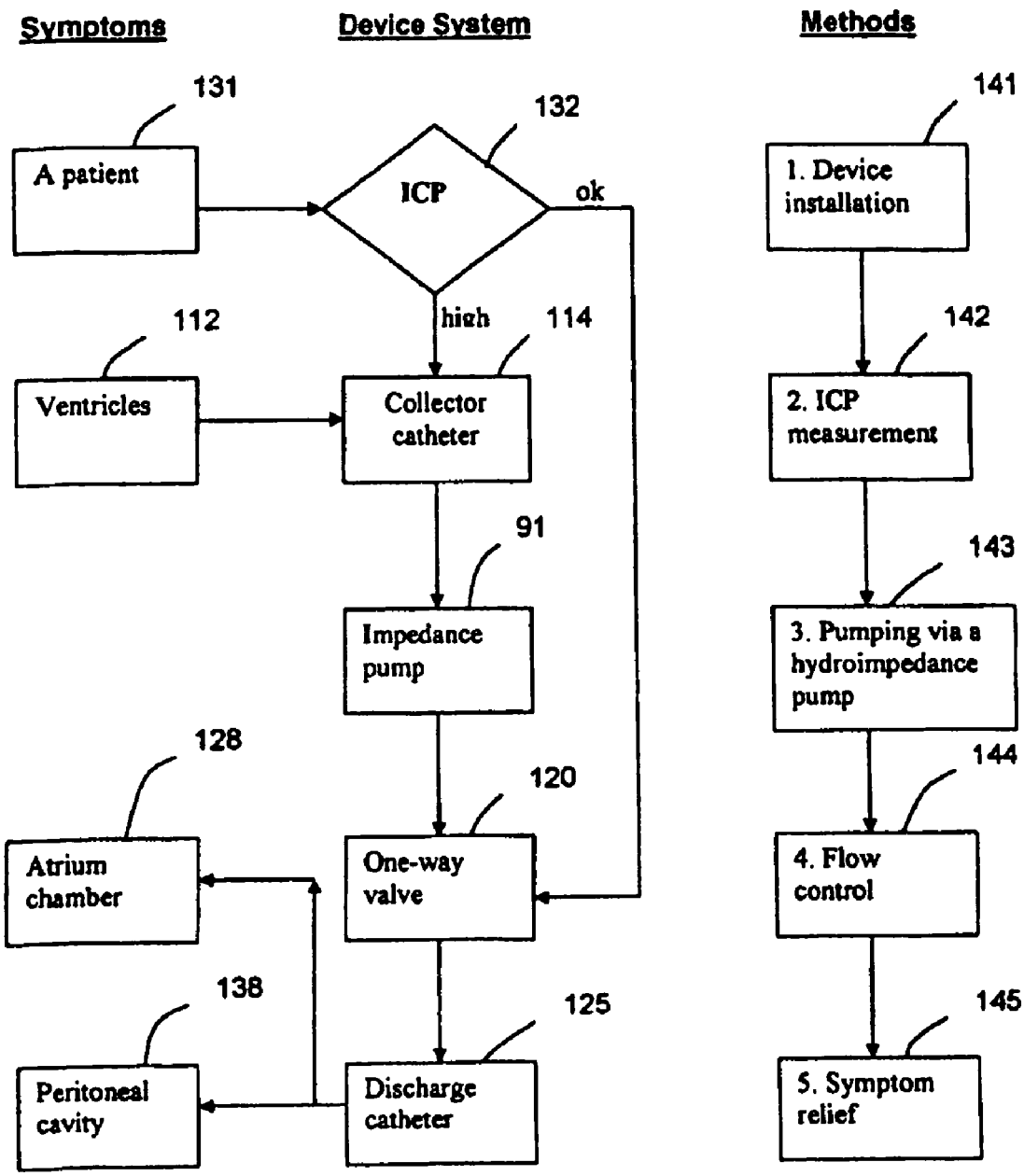
FIG. 19 shows a block diagram illustrating the operations of treating hydrocephalus of a patient.

FIG. 19 shows a block diagram of operation for treating hydrocephalus. A patient 131 with suspected hydrocephalus is treated by a physician. The ICP 132 from the ventricles 112 is measured or sensed as a parameter for adjusting the impedance pump 91 to control the CSF flow rate. When the ICP is higher than a predetermined value, the collector catheter 114 starts to withdraw CSF by the activated pump and drains the fluid through the discharge catheter 125 into either a peritoneal cavity 138 or atrium chamber 128. When the measured ICP of the ventricles is normal, the pump ceases to function and the one-way valve 120 prevents fluid from flow reversal. The methods may comprise steps of: device installation 141 into the appropriate location of the patient 131; ICP measurement 142 to trigger the drainage operations; pumping via a hydroimpedance pump 143 to lower the ICP; fluid flow control 144 to prevent siphoning; and fluid drainage to relieve symptoms of hydrocephalus 145.

Some aspects relate to a drainage system for draining body fluid from a cavity in the human body comprising in combination: a surgically implantable collector tube to receive fluid to be drained; a surgically implantable discharge tube to discharge fluid drained by the collector tube; and a surgically implantable impedance pump interconnecting the tubes, the pump is activated via a magnetic pinching mechanism. All of these implanted parts can be formed of flexible tubing.

Hydroimpedance Based Pumping

The embodiments described below relate particularly to a fluid pumping system based on the end segments with different hydroimpedances comprised, of the elastic tube element and an in-line pinching actuation of the elastic tube element.

The hydroimpedance, Z (or abbreviated as "impedance"), of the present system denotes frequency dependent resistance applied to a hydrofluidic pumping system.

Hydroimpedance pumps differ from traditional peristaltic pumping. Peristaltic pumping requires that the pump is pinched sequentially in order to move fluid unidirectionally. In an embodiment of the hydroimpedance pump, the pattern of pinching is determined by the pressure wave reflections that are required to sustain a pressure gradient across the pump. For example, with 3 pinching locations (shown in FIG. 7), this can be performed by pinching first the center, then together, the two outside locations. Pinching can alternatively be performed by pinching first the center, then the outside of the shorter section, followed by the outside of the longer section. These patterns are determined by the speed of the pressure wave, geometry of the pump, and the desired flow pattern to emerge from the pinching.

Another distinguishing aspect of the hydroimpedance pump from traditional peristaltic pumping is that for a given location of pinching, geometrical conditions and elastic properties of the pump only a narrow band of pinching frequencies and its harmonics will render unidirectional liquid pumping. In the traditional peristaltic pumping, the output increases when the frequency of the squeezing or pinching increases.

Impedance based pumping has also been recognized in nature. For example, the primitive vertebrate heart tube has been observed to pump blood even before the development of the endocardial cushions, the precursors to valve formation, In vivo observations of intracardiac blood flow in early embryonic stages of zebrafish (*Danio redo*) demonstrate that unidirectional flow through the heart, with little regurgitation, is still achieved despite the lack of functioning valves. Microscopy studies have shown that the mechanistic action of the pulsating heart tube does not appear to be peristaltic, but rather, a carefully coordinated series of oscillating contractions between the future ventricle and the outflow tract.

The basic prior art hydro elastic pump and its principles of operations is illustrated in FIG. 1. U.S. Pat. No. 6,254,355 to Gharib, the entire contents of which are incorporated herein by reference, discloses a pump comprising a first and a second elastic tube segment, the first tube segment having a fluidic characteristic which is different than the second tube segment, and a pressure changing element, which induces a pressure increase and a pressure decrease into the first and second tube segments in a way that causes a pressure difference between the first and second tube segments resulting in a pumping action based on the pressure difference.

In one aspect as shown in FIG. 1 (prior art in U.S. Pat. No. 6,254,355), an elastic tube 10 is shown in solid lines. The elastic tube 10 has a length L from a first end 17 to a second end 19. This tube can be connected at each of its two ends 17 and 19 to other connecting channels or tubes of any type or shape. The elastic tube 10 is divided into three segments, labeled A, C and B. Segment C is situated between segment A 13 and segment B 14. FIG. 1 shows segment C situated to provide an asymmetric fluid characteristic. In FIG. 1, the asymmetric characteristic is the result of geometric arrangement. As shown, the length of segment A is not equal to the length of segment B. Alternatively, the length of segment A can be equal to the length of segment B, but the elasticity or diameter of the two segments A and B may be different from one another. The purpose is to allow the pumping action to materialize according to the principles of the hydro elastic pump system.

Segment C provides a means of compressing the diameter of segment C to reduce its volume. The pinching can be a partial obstruction or a complete obstruction depending on the pinching amplitude. FIG. 1 shows partial compression distorting the tube to the area shown as dashed lines 11. In this respect, the pinching means 12 can be electromagnetic, pneumatic, electrostatic, piezoelectric, activated by shape changing alloys or polymers, and the like.

When segment C is compressed by the pincher 12, the volume within segment C is displaced to the segments A and B. This causes a rapid expansion of the volumes in segment A and segment B as shown and defined by the enclosure lines 11.

Since the segment B is shorter than segment A in this illustration, the volume expansion in segment B is more than the volume expansion in segment A. Since the same volume has been added to segments A and B, the cross-sectional radius or radius increase (Rb) of segment B will be larger than the corresponding radius or radius increase (RB) for segment A. The instant pressure inside each of these elastic segments or containers varies with the inverse of the cross-sectional radius of the curvature of the elastic tubes, by virtue of the Laplace-Young law of elasticity, $$P = \delta/R$$

Where P is the pressure, δ is the surface stress and R is the cross-sectional radius of curvature.

Therefore, liquid inside segment A will actually experience more pressure from the contracting force of the elastic tube wall. While this effect is counterintuitive, it is often experienced and appreciated in the case of blowing up a balloon. The beginning portions of blowing up the balloon are much more difficult than the ending portions. The same effect occurs in the asymmetric tube of this illustration as described. The instant pressure in segment A will actually be larger than the pressure in segment B.

If the constriction of segment C is removed rapidly, before the pressures in segment A and segment B equalizes with the total system pressure, the liquid in the high pressure segment A will flow toward the low pressure segment B. Hence, liquid flows from segment A towards segment B in order to equalize pressure. This creates a pumping effect.

The above illustration has described the timing and frequency of the pinching process. The size of the displaced volume depends on the relative size of segment C to the size of segments A and B. The ratios of C to A as well as the timing and frequency of the pinching set various characteristics of the pump. For example, a 5 cm long tube of 1 cm in diameter can be divided to segments A=3 cm, C=1 cm and B=1 cm. At a frequency of 2 Hz and duty cycle of 20% (close to open ratio), this tube can pump up to 1.8 liters/min.

To overcome the limiting drawbacks of an elastic tube pumping requiring different elastic properties of the segments A and B in a prior art hydro elastic pump system, a hydroimpedance pumping system that changes a shape of an elastic tube element in a way which increases the pressure in a first end member adjacent segment A more than that in a second end member adjacent the segment B to move fluid between the members based on a pressure differential, wherein the elastic tube element has same elastic properties of the segments A and B and has the first and second end members with different hydroimpedance attached to each end of segment A and segment B, respectively.

Figure 2:
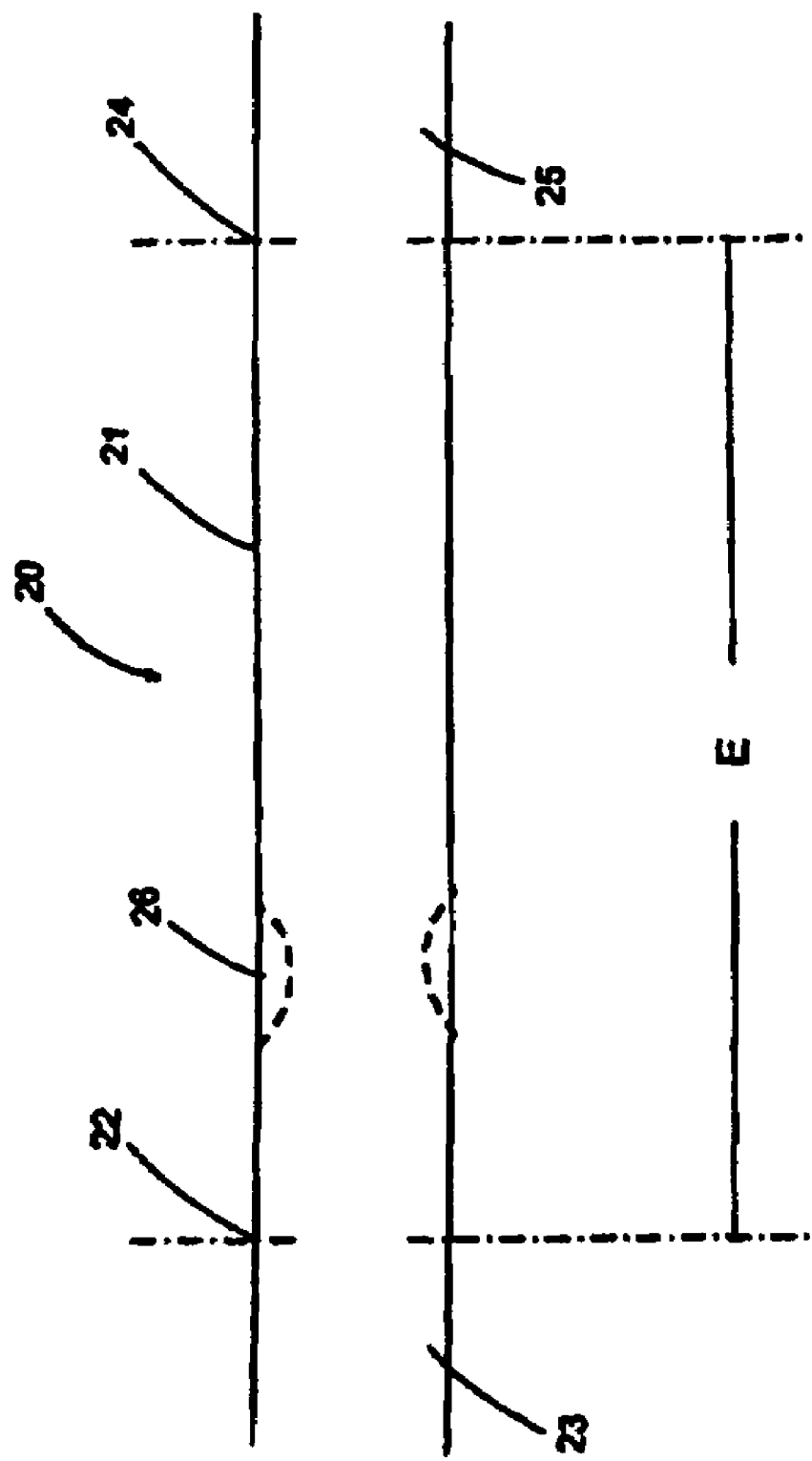
FIG. 2 is a basic hydroimpedance pump according to the principles of the present invention.

FIG. 2 shows a basic hydroimpedance pump. A hydroimpedance pump 20 comprises an elastic tube element 21 having two ends 22, 24 defining a length E. In one embodiment, the elastic properties or hydroimpedance of the elastic tube element 21 are essentially uniform along the full length E. In some aspect, the elastic element 21 of the present invention further comprises a first end member 23 attached to the end 22 of the elastic element 21 and a second end member 25 attached to the end 24 of the elastic element 21, wherein the lumen of the end members 23, 25 are in full fluid communication with the lumen of the elastic tube 21. The elastic tube element 21 has an impedance &whereas the end members 23 and 25 have impedances Zr and Zz, respectively. In general ZO is different from either Zi or ZZ. However, Zi can be equal to or different from Z2. The impedance, Z, of the present invention is a frequency dependent resistance applied to a hydrofluidic pumping system defining the fluid characteristics and the elastic energy storage of that segment of the pumping system. The FIGS. 4 through 7 describe various possible ways of achieving the proposed concepts and principles of the present invention.

FIGS. 3a-3e shows one possible sequence of flow directions with wave reflections for a basic hydroimpedance pump throughout the pinching cycle. In some aspects, the pump is made of a primary elastic section 21 of tubing connected by a first end member 23 having impedance Z1, and a second end member 25 having impedance Z2 that is different from Z1. FIGS. 3a-3e also shows the interfaces 22, 24 between the elastic section 21 and the end members 23, 25, respectively and the origin point 40 of the pinch-off by the pinching element 26. The elastic section 21 is then periodically pinchably closed, off-center from the interfaces 22, 24 to the end members 23,25 of different impedance. At a specific frequency and duty cycle, the pinching causes a net directional flow inside the tubing. Selecting a different frequency and duty cycle can reverse the direction of flow.

When the elastic section 21 is first pinched down at Time 0 at the origin 40, a high-pressure wave is emitted in both axial directions (arrows 41A, 42A) traveling at the same speed (FIG. 3a). When the pressure wave 41A encounters a shift in impedance at interface 22 at Time 1, a first portion 43A of the wave 41A continues to travel through and a second portion 44A of the wave is reflected back towards the origin 40 (FIG. 3b). The reflected portion 44A of the wave 41A eventually reaches the origin 40. Again at Time 2, when the pressure wave 42A encounters a shift in impedance at interface 24, a first portion 46A of the wave 42A continues to travel through and a second portion 45A of the wave is reflected back towards the origin 40 (FIG. 3c). The elastic section 21 may further be pinched a second time at Time 3 (FIG. 3d) with a high pressure wave emitted in both axial directions 41B, 42B.

In the hydroimpedance pump, the offset in location of the pinching and/or timing of the pinching cause the pressure waves to reflect at different intervals on the two sides. Depending on the selected frequency and duty cycle, the elastic section 21 of the primary tube will either be open or closed. If open, the wave will pass through to the other side of the tube. If closed, the wave will again be reflected back. As shown in FIG. 3e at Time 4, the pressure wave 41B encounters a shift in impedance at interface 22, and a first portion 43B of the wave 41B continues to travel through and a second portion 44B of the wave is reflected back towards the origin 40. At the same moment, the pressure wave 44A encounters a shift in impedance at interface 24, and a first portion 46B of the wave 44A continues to travel through and a second portion 45B of the wave is reflected back towards the origin 40. Similarly, another pressure wave 45A encountered a shift in impedance at interface 22 prior to Time 4 having a second portion 44C of the wave 45A reflected back passing the origin 40, while a first portion 43C of the wave 45A continues to travel through. A net pressure between the two sides of the pincher 26 can be created by timing the pinching in such a way that the reflected waves from one side pass through the origin 40, while the pressure wave from the other side are reflected back. There is a buildup of pressure on one side of the tube that causes a net flow to pass through (FIG. 3e).

For illustration purposes, consider the case where the pressure increases on the right hand side, the tube is initially squeezed causing a pair of pressure waves to traverse in both directions. The left-hand wave reflects on the left interface and passes through the origin. Before the right-hand wave returns to the origin, the primary tube is squeezed again. A new pair of pressure waves is released while the old waves are reflected to remain in the right-hand side. This can be repeated to continue to build up pressure. It is important, for the fluid to flow, that the pump remains open as long as possible while maintaining the pressure gradient.

Figure 4:
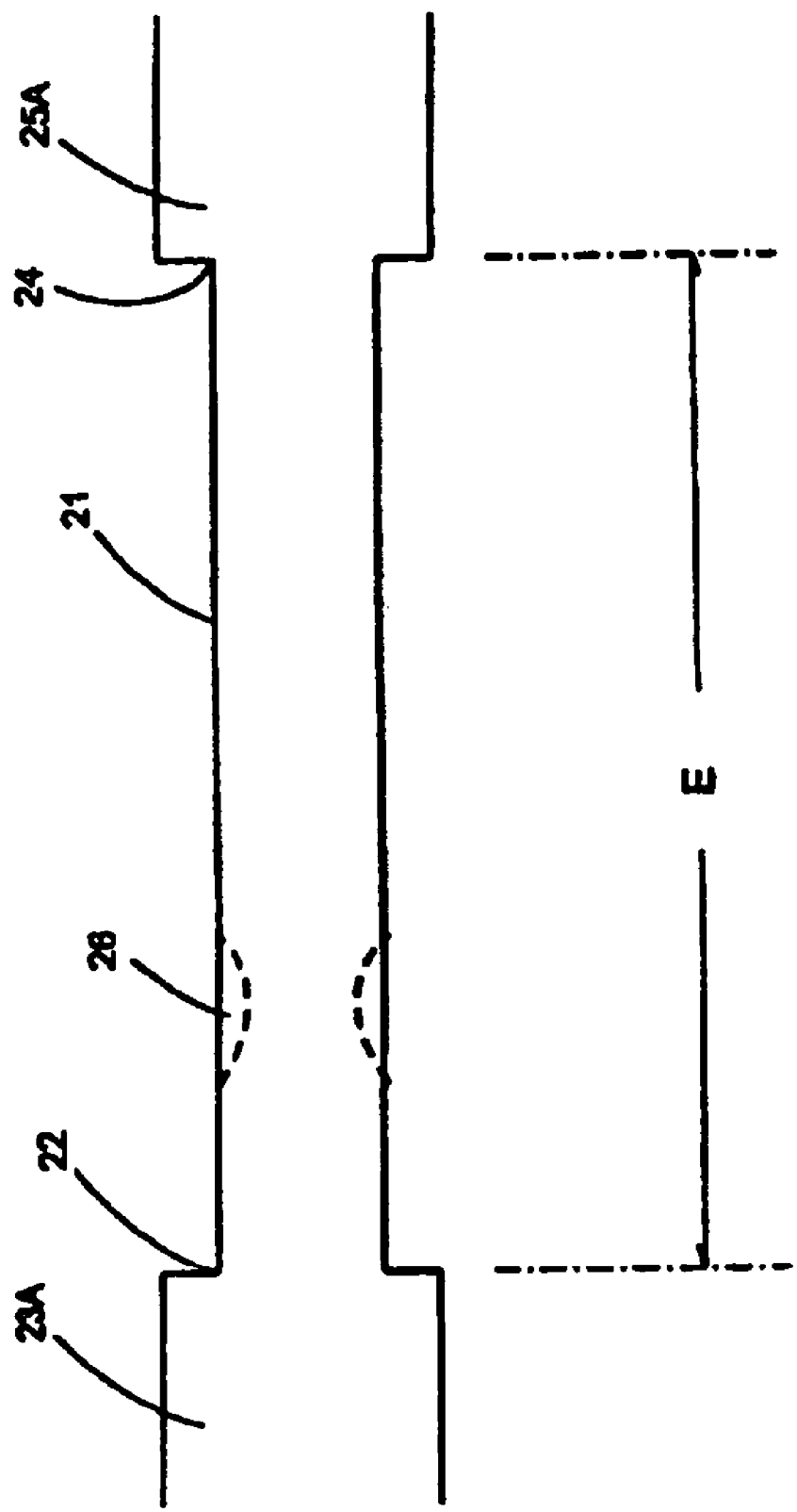
FIG. 4 is one embodiment of attaching at least one end member of larger diameter or dimension at the ends of the elastic tube element.
Figure 5:
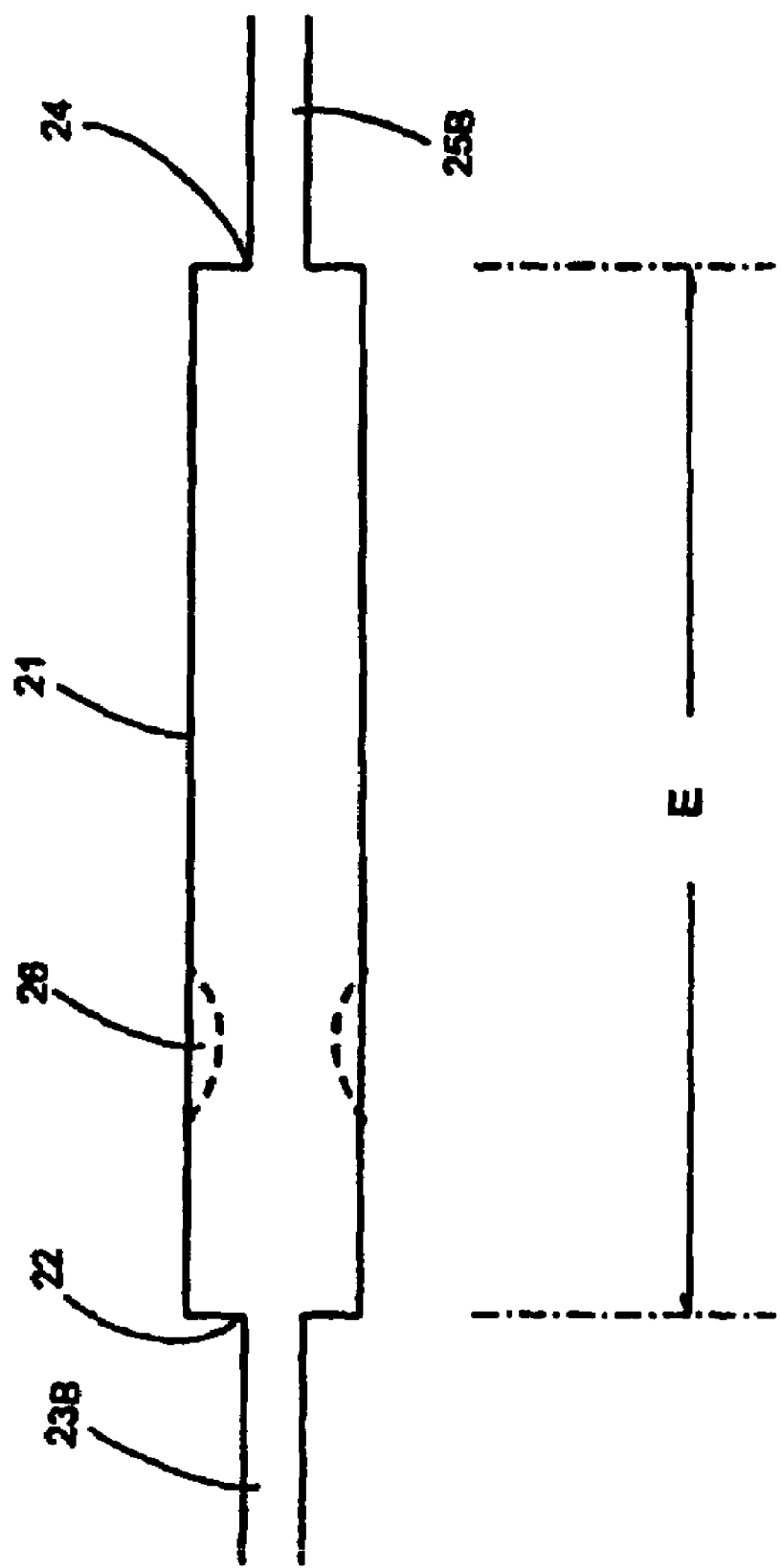
FIG. 5 is another embodiment of attaching at least one end member of smaller diameter or dimension at the ends of the elastic tube element.

In one aspect, FIG. 4 shows an embodiment of attaching at least one end member 23A, 25A of larger diameter or dimension at the ends 22 and 24, respectively of the elastic tube element 21, wherein the lumen of the end members 23A, 25A are in full fluid communication with the lumen of the elastic tube 21. The expansion members 23A, 25A can have the same or different compliance, elastic properties, or impedance from that of the elastic tube element 21 or from each other. The end members can have the same or different wall thickness from that of the elastic tube element or from each other. Further, the expansion member 23A, 25A can have different cross-sectional geometry from that of the elastic tube element 21 or from each other, In another aspect, FIG. 5 shows an embodiment of attaching at least one end member 23B, 25B of smaller diameter or dimension at the ends 22, 24 of the elastic tube element 21, wherein the lumen of the end members 23B and 25B are in full fluid communication with the lumen of the elastic tube 21. The restriction member 23B, 25B can have the same or different compliance, elastic properties or impedance from that of the elastic tube element 21 or from each other. The end members can have the same or different wall thickness from that of the elastic tube element or from each other. Further, the restriction member 23B, 25B can have different cross-sectional geometry from that of the elastic tube element 21 or from each other.

Figure 6:
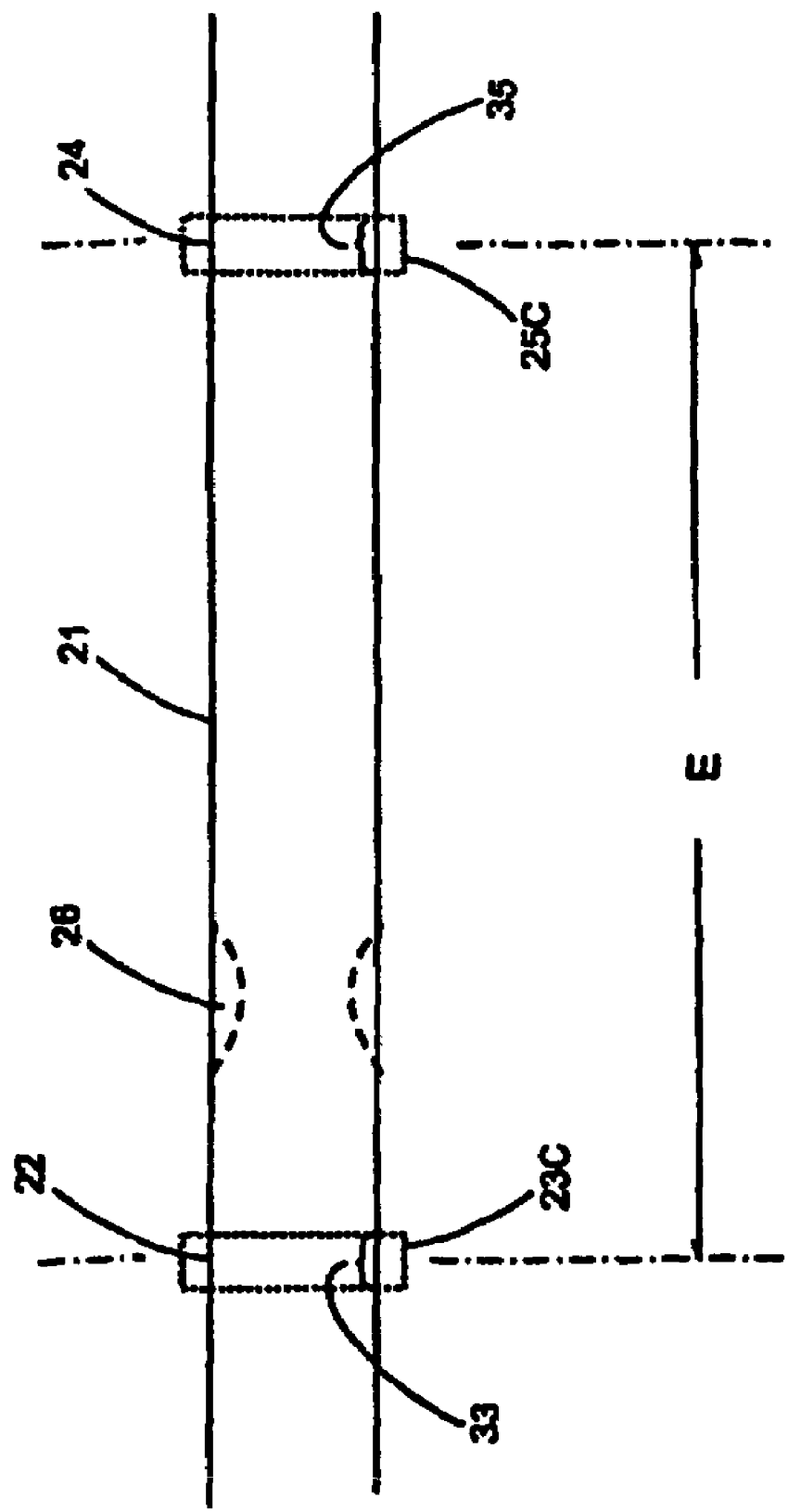
FIG. 6 illustrates one aspect of dynamically changing the conditions of the end member at the ends of the elastic tube element.

FIG. 6 illustrates one aspect of dynamically changing the conditions of the external tube or chamber 23C mounted over a first flexible wall segment 33 at the end 22 of the elastic tube element 21, whereas the external tube or chamber 25C is mounted over a second flexible wall segment 35 at the end 24 of the elastic tube element 21. The pumping is initiated and operated by stiffening or softening the flexible wall segments synchronously or asynchronously with the pinch-off process using a pinching element or means 26. By selectively applying external pressure through the external chambers 23C, 25C to the flexible wall segments 33 and 35, it is provided a hydroimpedance pumping system comprising changing a shape of an elastic element in a way which increases the pressure in the first flexible wall segment 33 more than that in the second flexible wall segment 35 to move fluid between the two segments based on pressure differential, wherein the elastic element 21 has the first flexible wall segment 33 and the second flexible wall segment 35 with different hydroimpedance attached to the ends 22 and 24 of the elastic element 21, respectively. The applying of external pressure can be achieved by other techniques, such as imbedded memory alloys or magnetic fields.

Figure 7:
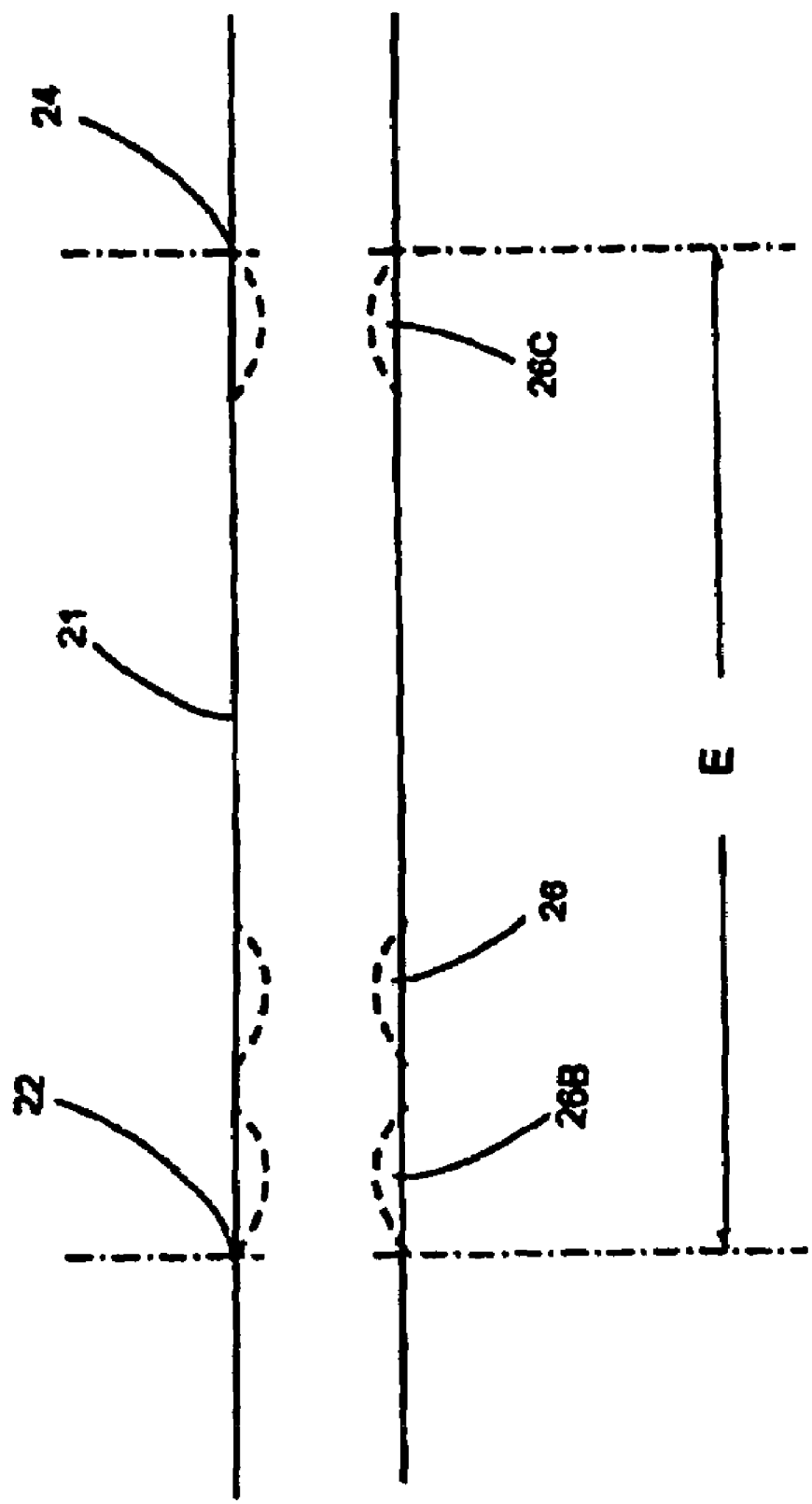
FIG. 7 illustrates another aspect of actively actuating the conditions of the elastic tube elements with multiple pinch-off actuators.

FIG. 7 shows another illustration of actively actuating the conditions of the elastic tube element 21 with multiple pinch-off actuators (that is, pinching elements or means) 26B, 26C, in addition to the main pinching element or means 26. By positioning the auxiliary pinching elements 26B, 26C that are capable of producing partial or complete pinch-off at the end positions 22, 24 to reflect waves generated by the main pinching element 26, a hydroimpedance pumping system allows changing a shape of an elastic element in a way which increases the pressure by the first auxiliary pinching element 26B at the first end 22 more than the pressure by the second auxiliary pinching element 26C at the second end to move fluid between the two ends based on pressure differential.

In another aspect, a pump has an elastic element having a length with a first end and a second end, a first pressure changing element disposed at about the first end and a second pressure changing element disposed at about the second end. The pump further comprises pressure change means for inducing a pressure increase and a pressure decrease into the first and second ends, in a way which causes a pressure difference between the first and second ends, and causes a pumping action based on the pressure difference, wherein the first and second pressure changing elements are capable of producing partial or complete pinch-off to reflect waves generated by the pressure change means.

The elastic tube element 21, the end members 23,25,23A, 25A, 23B, 25B, or the end wall segments 23C, 25C of the present embodiment may be made of a material selected from a group consisting of silicone (e.g., Silastic™, available from Dow Corning Corporation of Midland, Mich.), polyisoprene, polyurethane (e. g., Pellethane™, available from Dow Corning Corporation), polyether block amide, polyvinyl alcohol, polyvinyl pyrolidone, fluorinated elastomer, polyethylene, polyester, and combination thereof. The material is preferably biocompatible and/or hemocompatible in some medical applications. The elastic tube element and the end members need not be round, but could be any shaped cross section.

In yet another aspect, the pinching element or actuating means 26 may comprise pneumatic, hydraulic, magnetic solenoid, polymeric, or an electrical stepper or DC motor. The pseudo electrical effect could be used for actuating means. The contractility of skeletal, or heart muscle, as well as active polymer-based materials or magnetic fluids may also be used. The actuating means or system may use a dynamic sandwiching of the segments or members similar to the one cited in U.S. Pat. No. 6,254,355, as will be apparent to those of skill in the art. In some aspects, a hydroimpedance pumping system changes a shape of an elastic element in a way which increases the pressure in the first end member 23B more than that in the second end member 25B to move fluid between the two members based on pressure differential, wherein the elastic element 21 has the first member 23B and the second member 25B with different hydroimpedance attached to the ends 22 and 24 of the elastic element 21, respectively.

The pinching means, pinching element or pinch-off actuator 26, 26B, 26C be pneumatic, hydraulic, electromagnetic, polymeric, inductor driven 47, an electrical stepper, a DC motor, the contractility of skeletal, or heart muscle, active polymer-based materials or magnetic fluids. A number of different alternatives are also contemplated and are incorporated herein. This system without the limiting drawbacks of prior art hydroelastic tube pump that requires different elastic properties of the segments along the elastic tube can be used effectively for pumping blood. This can provide a more reliable pumping operation, since any mechanical constrictions in the blood stream provide a potential site for mechanical failure as well as sedimentation of formed blood elements and thrombosis. Hence, this system, which utilizes the hydroimpedance features but does not require a valve system, can be highly advantageous.

The pump system of the embodiment may include a feedback system with a flow and pressure sensor, which is well known to one who is skilled in the art. In one aspect, the pinching element 26 can be located at any particular position along the length E of the elastic element 21 and may be driven by a programmable driver which also provides an output indicative of at least one of frequency, phase and amplitude of the driving. The values are provided to a processing element, which controls the timing and/or amplitude of the pinching via feedback. The relationship between timing, frequency and displacement volume for the compression cycle can be used to deliver the required performance. The parameters ZO, Zr and Z2, as well as the tube diameter, member diameters, and their relative elasticity can all be controlled for the desired effect. These effects can be determined by trial and error, for example.

For clinical applications, one can use the given patient's variables to determine the pump parameters that are based on the patient's information. One aspect allows changing a shape of an elastic element in a way which increases the pressure in the first end member 23A more than that in the second end member 25A to move fluid between the two members based on pressure differential, wherein the elastic element 21 comprises the first member 23A and the second member 25A with different hydroimpedance attached to the end 22 and 24 of the elastic element 21, respectively.

In another aspect, the pinching of the elastic element is carried out by compressing a portion of the elastic element, where the pinching is powered by electricity that is converted from body heat based on Peltier effects, from mechanical motion of muscles based on piezoelectric mechanism, or from a remote battery or solar cells.

EXAMPLE NO. 1

A micro hydroimpedance pump according to the principles described above is used to demonstrate impedance based pumping on a microscale.

FIG. 2 shows elements of the pump 20 employing a semicircular elastic channel 21 with a cross section area 750 (μm)$^2$ made of silicone rubber with a Young's modulus at about 750 kPa. The supporting substrate is a glass cover slide to allow optical viewing.

The actuator 26 is a 120 μm-wide and 15 μm-high channel crossing the fluid channel with a thin membrane of about μm in between. When activated pneumatically, the actuator/pincher 26 squeezes one side of the fluid channel wall at a controllable frequency at 10 Hz for the current arrangement. The red food coloring with small-suspended particles was added to simulate the blood and show the pumped liquid boundaries. The end members 23, 25 with impedance mismatch ($Z_1$, for the end member 23, $Z_0$ for the end member 25, and $Z_0$ for the elastic channel 21) for the purpose of wave reflection are provided through stiffer materials at the interfaces 22, 24. The frequency of the pinching was scanned. For the above-mentioned micro hydroimpedance pump setup, the optimum frequency for the maximum pumping flow rate was about 10 Hz. The pump rate vs. frequency graph looks like an asymmetric bell. The maximal speed achieved is about 2 mm/second with a flow rate about 0.1 pL/min. The optimum frequency was very sensitive to the material properties, wall thickness, and the length of the segments.

EXAMPLE NO. 2

A micro hydroimpedance pump is used to demonstrate the feasibility of creating non-substrate based micropumps for limited space applications. The pump is comprised of an elastic section with a cross sectional area of about 2.8 mm$^2$, connected to a rigid glass section with an area of about 0.5 mm$^2$ connected. The elastic section of the pump is made out of silicone rubber with a Young's modulus at about 220 kPa. Wave reflections are created by an impedance mismatch provided through pinching asymmetrically with respect to the stiffer materials at the interfaces. The input waveform to the coil was a square wave of 48 mA with a −24 mA offset.

FIG. 17 shows an example of the hydroimpedance pump frequency response in terms of flow velocity, and input oscillation frequency on the elastic tube. The flow direction is indicated by the positive flow rate in one direction and the negative flow rate in an opposite direction. By operating a. frequency range from 0 to about 140 Hz, the flow rate could range from −2.85 ml/min at 33 Hz to +15.15 ml/min at 76 Hz frequency. The frequency for any desired flow rate and flow direction was sensitive to the material properties, wall thickness, and the length of the segments.

Figure 8:
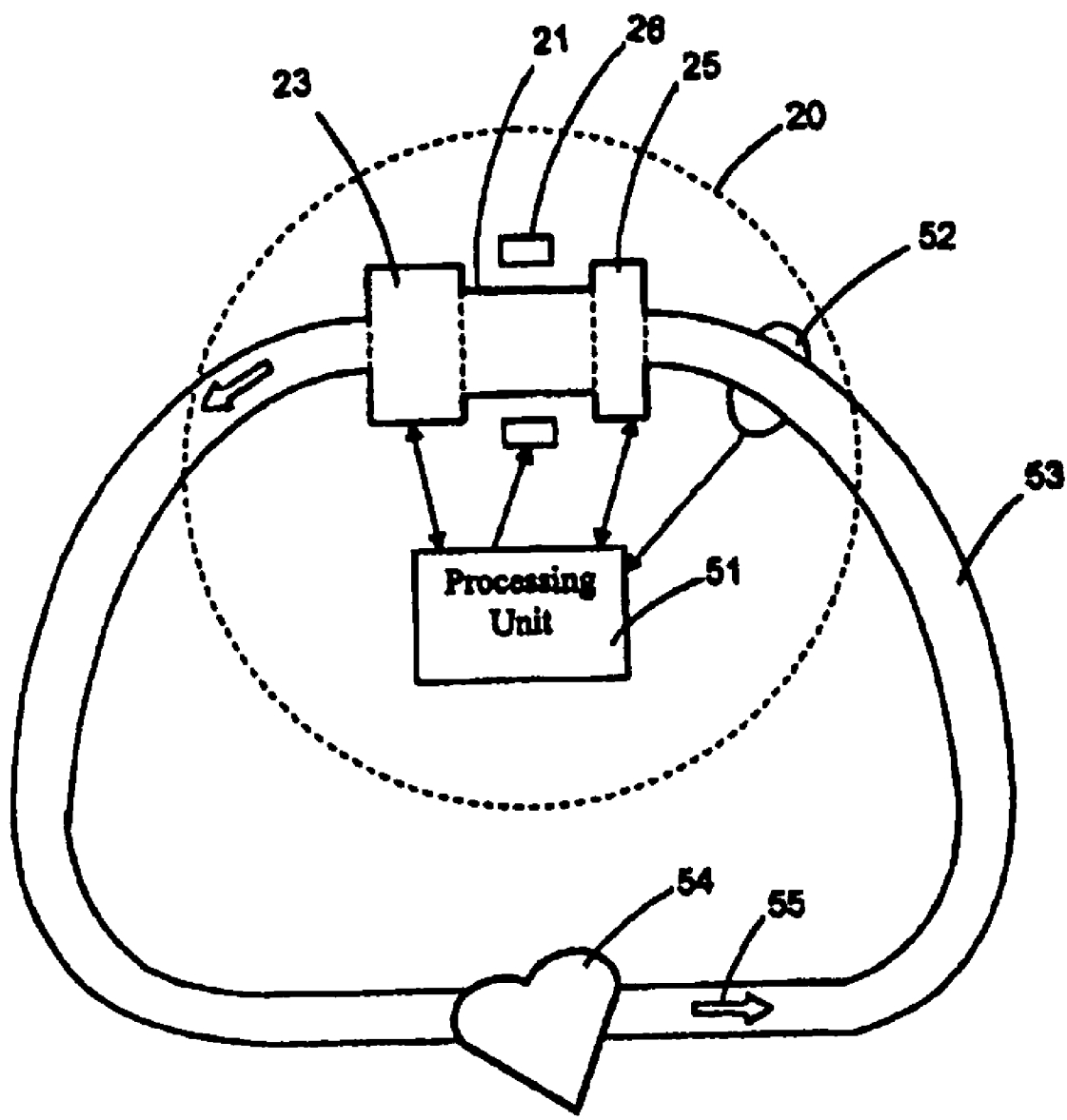
FIG. 8 shows a simulated diagram of the hydroimpedance pump system in operation.

FIG. 8 shows a simulated diagram of the hydroimpedance pump system in operation. In this embodiment, the flow circuit comprises a pump system 20 having a feedback control processing unit 51 to initiate and regulate the blood flow through a simulated diseased heart 54, The pipe 53 as described herein, can be the pipe through which the fluid is flowing (in a direction shown by an arrow SS), such as the aorta. The pump system 20 comprises an elastic tube element 21 having two end members 23,25, wherein the elastic properties of the elastic tube element 21 are substantially uniform along the full length between the end members. The elastic tube element 21 has an impedance $Z_0$ whereas the end members 23 and 25 have impedances $Z_1$ and $Z_2$, respectively. In general $Z_0$ is different from either $Z_1$ or $Z_2$. The impedance, Z is a frequency dependent resistance applied to a hydrofluidic pumping system defining the fluid characteristics and the elastic energy storage of that segment of the pumping system.

The feedback system includes a flow and pressure sensor 52. The pinching element 26 is driven by a programmable driver or other means which is incorporated in or attached to the processing unit 51, wherein the unit 51 displays the flow/pressure data and at least one of frequency, phase and amplitude of the driving. The values as provided control the timing, frequency and/or amplitude of the pinching via feedback. The relationship between timing, frequency, and displacement volume for the compression cycle can be used to deliver the required performance. For the clinical applications, one can use a patient's variables and find the pump parameters that are relevantly based on the patient's information.

Figure 9A:
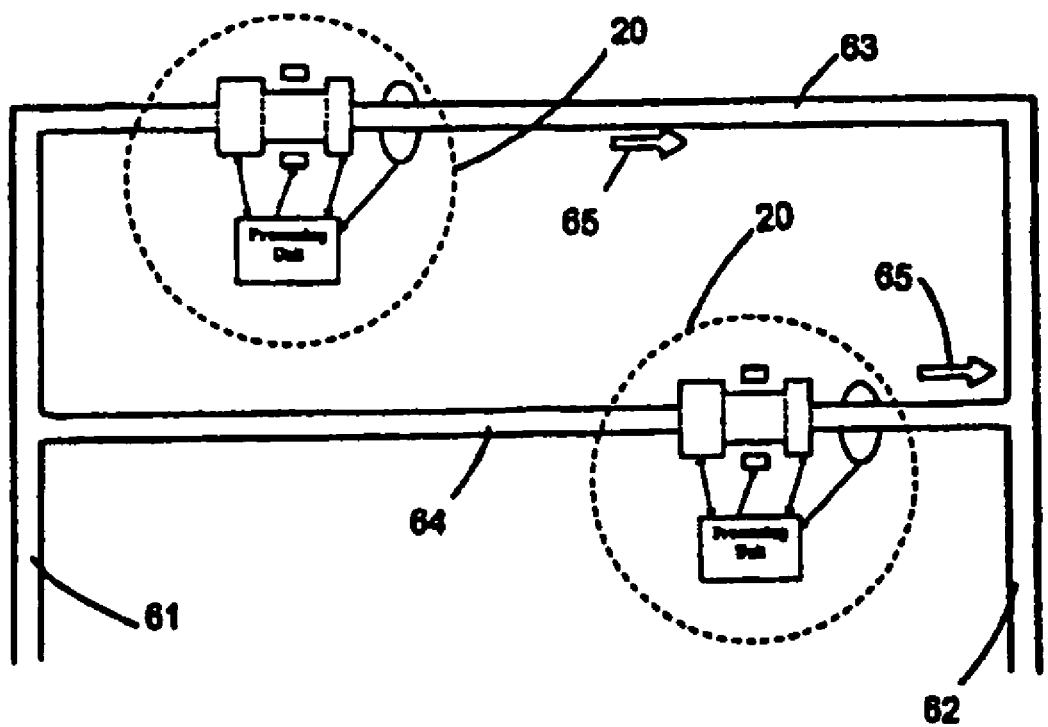
FIG. 9A shows one embodiment of operations by combining a plurality of hydroimpedance pump systems in parallel.
Figure 9B:
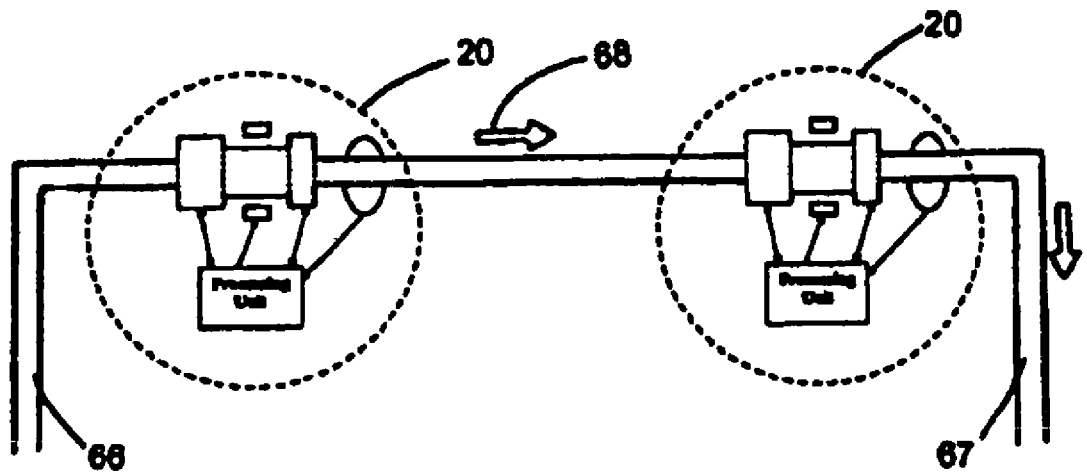
FIG. 9B shows another embodiment of operations by combining a plurality of hydroimpedance pump systems in series.
Figure 9C:
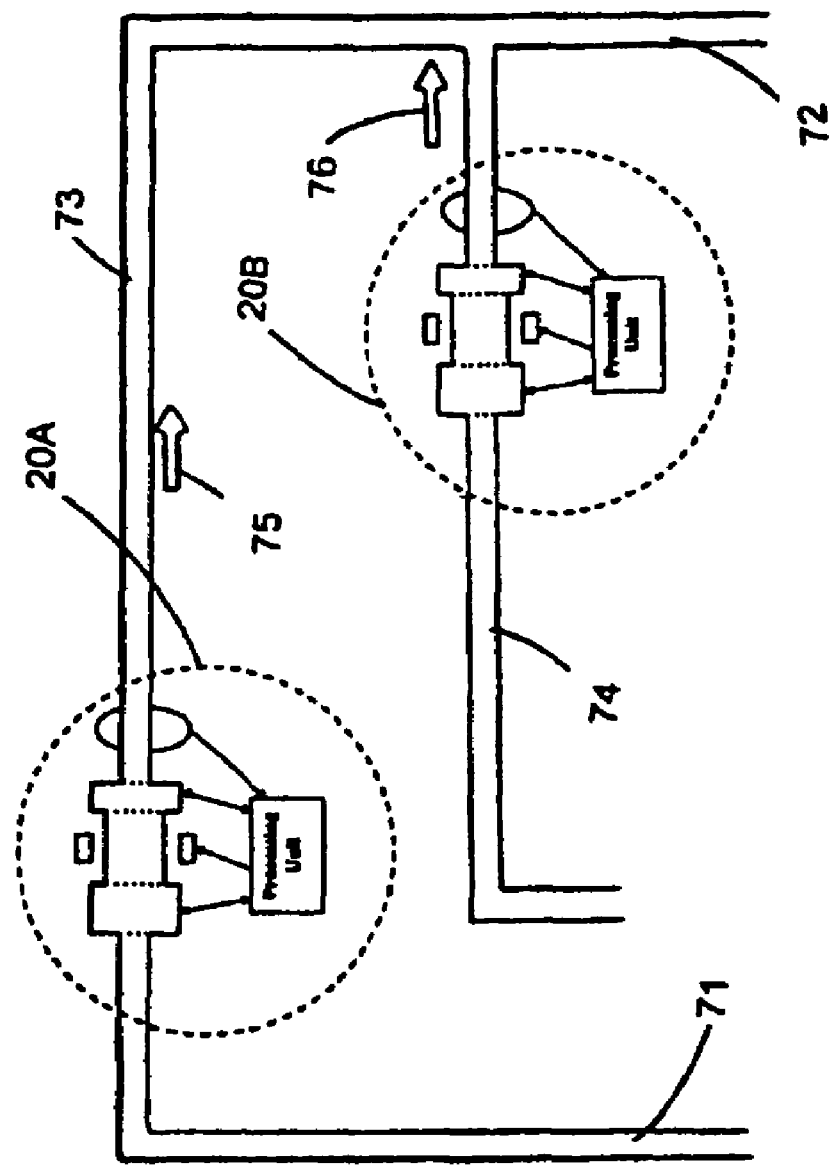
FIG. 9C shows still another embodiment of operations by mixing a plurality of hydroimpedance pump systems.
Figure 10:
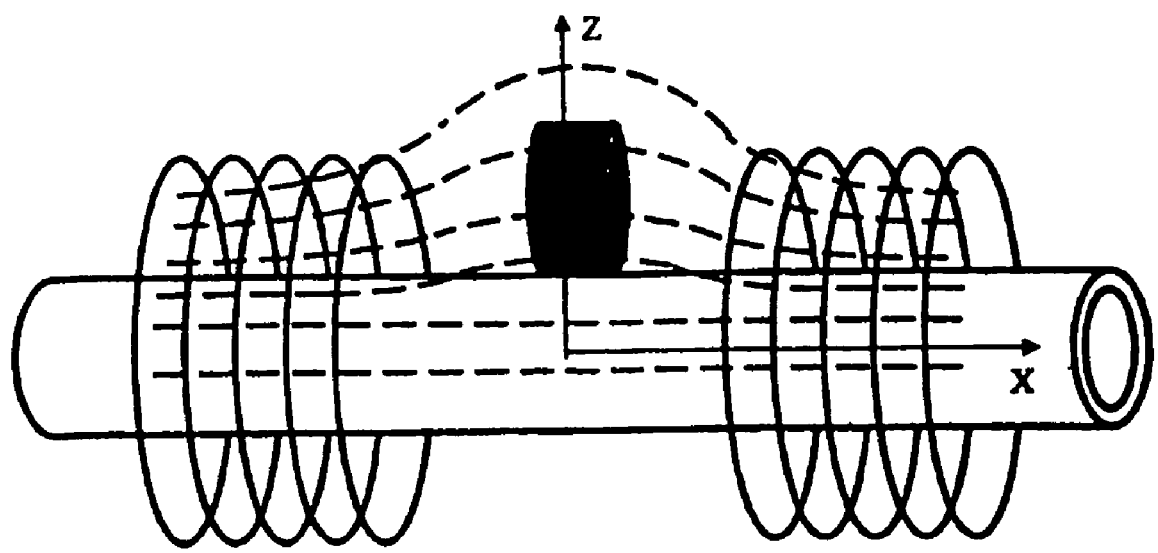
FIG. 10 shows a schematic coil-magnet configuration used in a hydroimpedance pump according to the principles of the invention.
Figure 11:
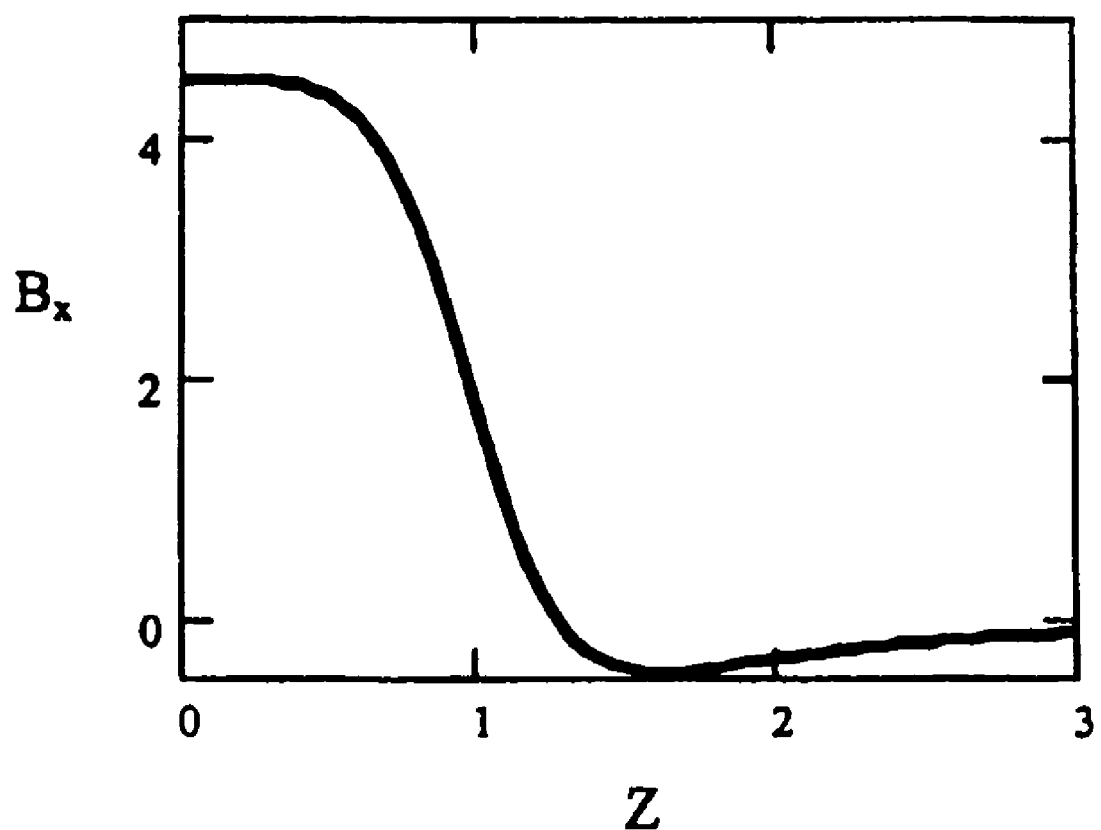
FIG. 11 shows a graphical representation of the value of the x-component of the magnetic field along the z-axis centered in between the two coils of FIG. 10.
Figure 12:
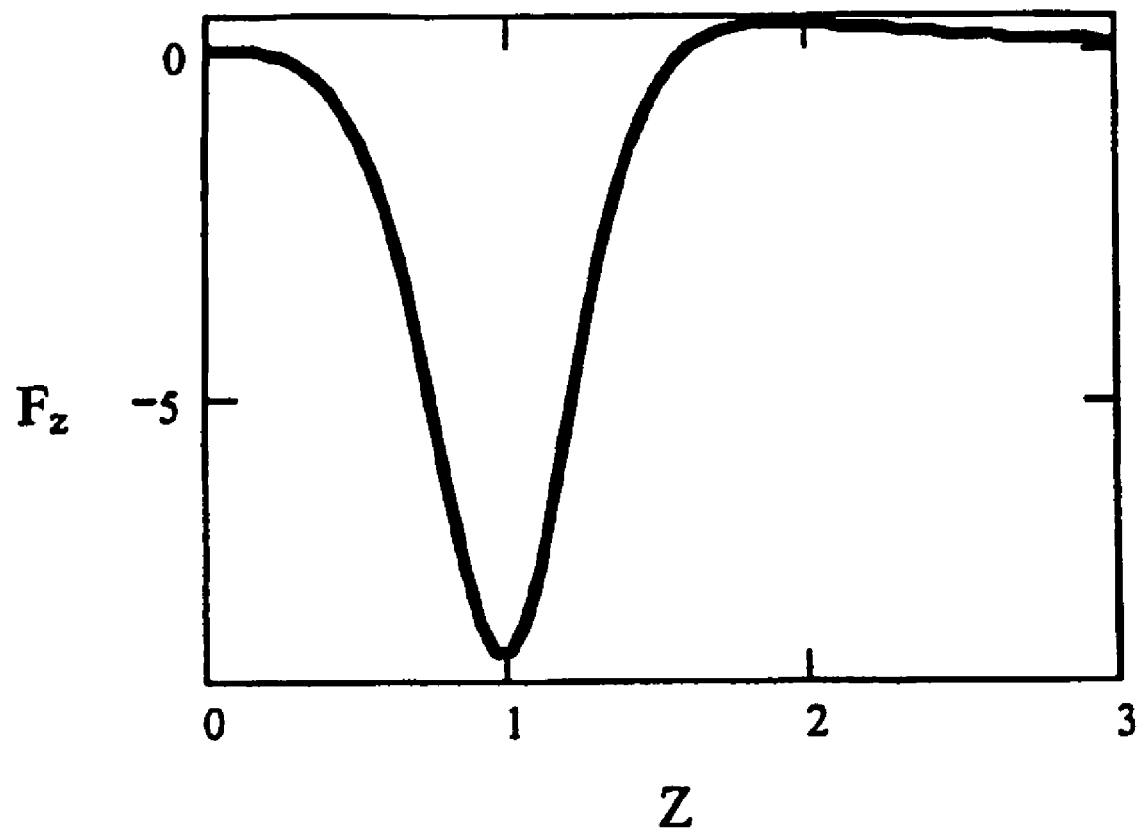
FIG. 12 shows the force on the magnet along the z-axis from the in-line coil configuration of FIG. 10.
Figure 13A:
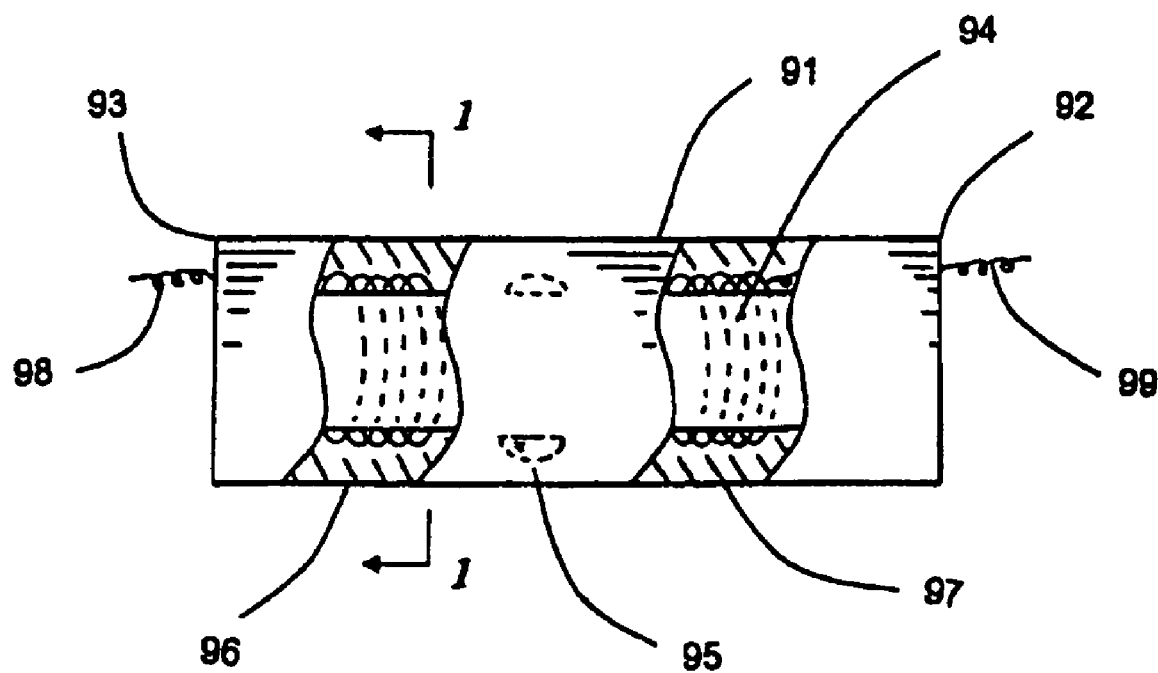
FIG. 13A shows a hydroimpedance pump comprising in-line magnetic pinching elements in an elastic element according to the principles of the invention.
Figure 13B:
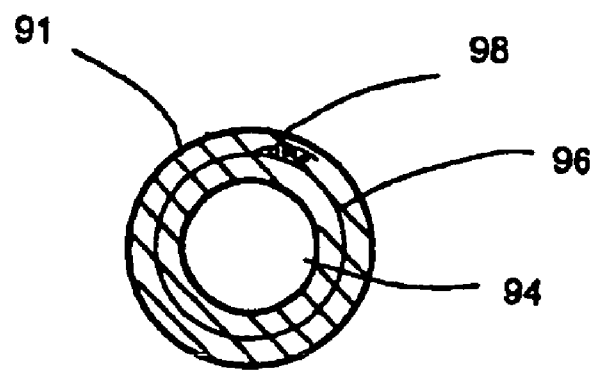
FIG. 13B shows a cross-sectional view, section 1-1 of the hydroimpedance pump of FIG. 13A.

FIGS. 9A, 9B, and 9C show various modes of operations. In an embodiment as shown in FIG. 9A, the flow system directs fluid from a first point 61 to a second point 62 is facilitated by a combination of a plurality of hydroimpedance pump systems 20 in parallel, each system pumping fluid 63, 64 in the arrow direction 65. In another embodiment as shown in 9B, the flow system from an upstream point 66 to a downstream point 67 (as shown by an arrow 68) is facilitated by a combination of a plurality of hydroimpedance pump systems 20 in series.

In another embodiment as shown in FIG. 9C, the flow circuit system directing the fluid from a first point 71 to a second point 72 is enhanced by a branching-in mixing of a second hydroimpedance pump systems 20B into the first hydroimpedance pump system 20A, wherein the first system 20A pumps fluid 73 in the arrow direction 75 while the second system 20B pumps fluid 74 in the arrow direction 76. In this case, the total flow volume at the second point 72 is higher than that at the first point 71. In another embodiment, the flow 74 of the second hydroimpedance pump system 20B may be reversed (as opposite to the flow direction 76) for branching-out diversion of the first flow 73. In this case, the total flow volume at the second point 72 is less than that at the first point 71. In summary, a pumping circuit system by combining a plurality of the hydroimpedance pump systems 20, 20A, 20B in any mode of parallel, series, branching-in, branching-out, or combination thereof is useful in certain medical applications.

Figure 14A:
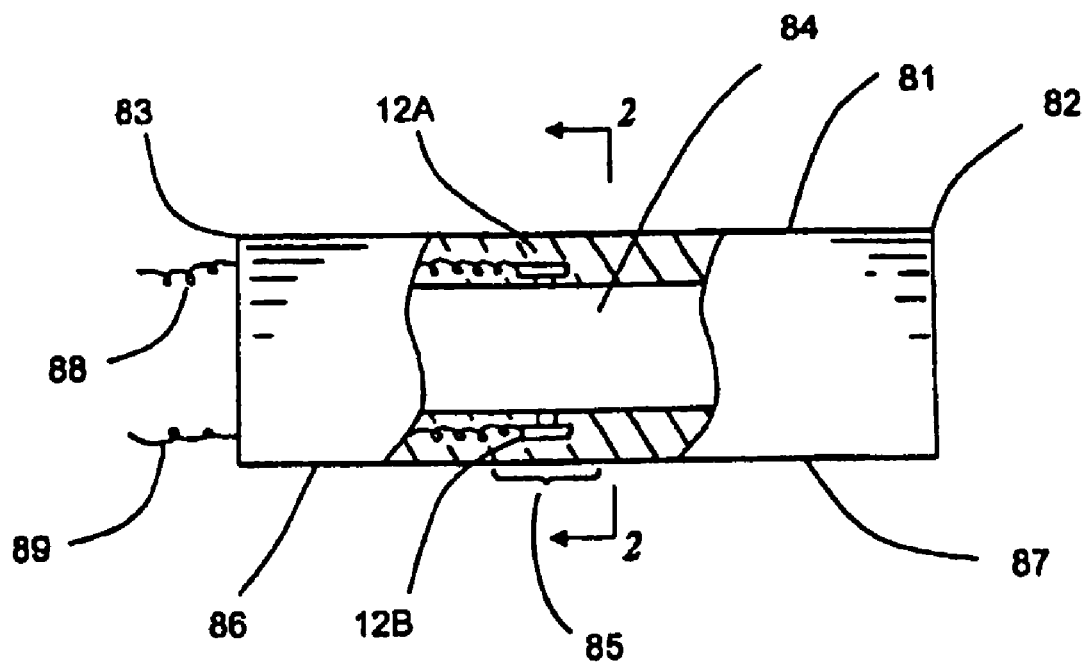
FIG. 14A shows a simulated diagram of the hydroimpedance pump system with an in-line pinching element in the elastic tube.
Figure 14B:
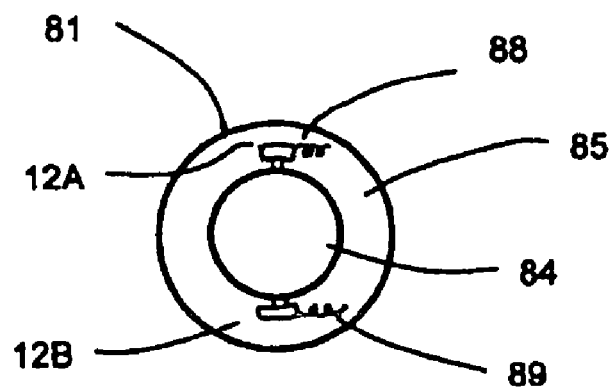
FIG. 14B shows a cross-sectional view, section 2-2 of the hydroimpedance pump of FIG. 14A.

FIG. 14A shows a simulated diagram of the hydroimpedance pump system 81 with one possible pinching configuration 12A, 12B embedded in the elastic element 85, whereas FIG. 14B shows a cross-sectional view, section 2-2 of the hydroimpedance pump of FIG. 14A. In one embodiment, a valveless pump of the invention comprises an elastic element having a lumen 84 and a length with a first end member 86 and a second end member 87, wherein the first end member 86 has a first end 83 configured for connecting to a flow output terminal and the second end member 87 has a second end 82 configured for connecting to a flow input terminal, and wherein the first end member has an impedance different from an impedance of the second end member; and pressure change means for inducing a pressure increase and a pressure decrease into the first and second end members by compressing a portion of the elastic element with an inline pinching element 12A or 12B, in a way which causes a pressure difference between the first and second end members, and causes a pumping action based on the pressure difference. The pinching elements are powered by conductors 88 and 89 from a power source, such as a battery, a solar cell arrangement, an electric generator, a piezoelectric converter, and the like. In one embodiment, the pinching elements 12A, 12B and the electrical conductors 88, 89 are mounted along the wall or embedded within the wall of the fluidic conduit. In a further embodiment, the hydroimpedance pump as shown in FIG. 14 or the like can be percutaneously delivered to and deployed in a patient by a deployment catheter or cannula.

Figure 15:
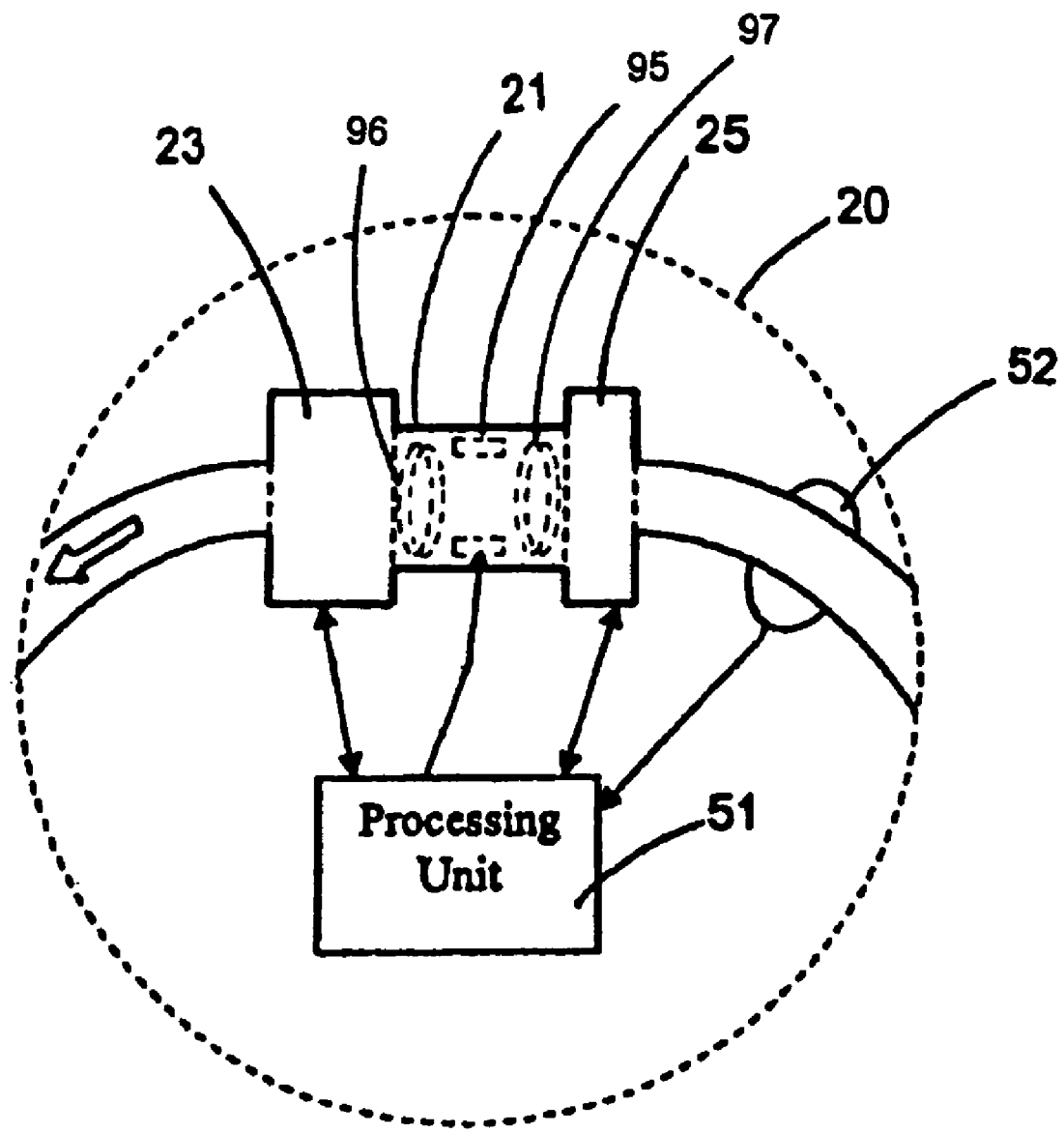
FIG. 15 shows a simulated diagram of the hydroimpedance pump system in operation with magnetic pinching mechanism.

FIG. 15 shows a simulated diagram of the hydroimpedance pump system in operation with a magnetic pinching mechanism. In one embodiment, the flow circuit comprises a pump system 20 having a feedback control processing unit 51 to initiate and regulate the flow. The feedback system includes a flow and pressure sensor 52. The pump system 20 comprises an elastic tube element 21 having two end members 23, 25, wherein the elastic properties of the elastic tube element 21 are essentially uniform along the full length between the end members. The elastic tube element 21 has an impedance ZO whereas the end members 23 and 25 have impedances $Z_1$ and $Z_2$, respectively.

The tubular hydroimpedance pump as disclosed can possess internal diameters of any dimension, however preferably in the range of 5 microns to 2 cm. The external or outside diameter can as well be of any dimension however preferably in the range of about 7 microns to 20 centimeters. The length of the pump also may be of any length however preferably in the range of about 10 microns to several meters.

Although only a few embodiments have been disclosed in detail above, other modifications are possible, and this disclosure is intended to cover all such modifications, and most particularly, any modification which might be predictable to a person having ordinary skill in the art. For example, while the above has described specific pumping mechanisms, other pumping mechanisms are also possible.

Also, only those claims which use the words "means for" are intended to be interpreted under 35 USC 112, sixth paragraph. Moreover, no limitations from the specification are intended to be read into any claims, unless those limitations are expressly included in the claims.

What is claimed is:

1. A method, comprising:
    pumping in a human body, using a collector tube having a tip section, a discharge tube having an end section, and a tube shaped element between said collector tube and said discharge tube, said pumping including pinching at least one portion of said tube shaped element to pump fluid from said collector tube to said discharge;
    sensing a pressure in a body cavity and producing an output indicative of the sensed pressure; and
    controlling said pinching based on said output indicative of the sensed pressure, to control an amount of said pumping using an automated controller to create plural pressure waves, which are reflected, said controlling creating said pressure waves at a first frequency and duty cycle to sum said pressure waves and said reflected pressure waves by controlling said pinching to create a new pressure wave at a time when another wave is reflected to a location of said pinching, to pump fluid within the human body in a first direction from said collector tube to said discharge tube.

2. A method as in claim 1, wherein said tube shaped element is a hydroimpedance pump formed of a length of tube that has different characteristics than at least one of said collector tube and/or said discharge tube, and actuating by pressing against and constricting an internal cross-sectional area of said length of tube.

3. A method as in claim 2, wherein said using comprises initiating a pumping action of the hydroimpedance pump by pressing against the tube.

4. A method as in claim 2, wherein the hydroimpedance pump is formed by first and second sections of elastic tube, having different elastic impedances from one another.

5. A method as in claim 4, wherein one of said sections of elastic tube comprises at least one of said collector and discharge tubes.

6. A method as in claim 2, further comprising sensing characteristics of fluid movement, and wherein said control an amount of said pumping is based on the sensed characteristics.

7. A method as in claim 6, wherein said adjusting an amount of the pumping comprises changing a frequency of the pumping.

8. A method as in claim 2, wherein said tube shaped pump comprises a plurality of separate pumping portions, each of which are separately operable to pump fluid.

9. A method as in claim 8, wherein said plurality of separate pumping portions comprise a plurality of pumping portions which are located in series with one another.

10. A method as in claim 8, wherein said plurality of separate pumping portions comprise a plurality of pumping portions which are located in parallel with one another.

11. A method as in claim 2, wherein said actuating comprises using includes a first actuator part pressing against and capable of at least partially constricting a first portion of said length of tube, and a second actuator part, pressing against and capable of at least partially constricting a second portion of said length of tubing, spaced from said first portion of said length of tubing, and wherein said controlling comprises controlling said first and second actuator parts to sum said pressure waves using a pattern of pinching said first actuator part and said second actuator part that sustain a pressure gradient in a way that lowers body cavity pressure.

12. A method as in claim 11, wherein at least one of said actuators completely constricts said tube during said pumping based on said output.

13. A method as in claim 1, further comprising detecting an orientation of said shunt system, and using a valve to close a fluid flow, based on said orientation.

14. A method as in claim 1, wherein said tube shaped pump is a hydroimpedance pump, and said actuating comprises stiffening and softening at least one portion of a wall of said pump.

15. A catheter shunt system, comprising:
    a first collector catheter;
    a second, discharge catheter;
    a pump, formed of a length of tubing, and connected to said first and second catheters, and allowing pumping of fluid from said first catheter to said second catheter;
    a pinching mechanism to create plural pressure waves in said length of tubing, which are reflected;
    a body cavity pressure sensor that senses a pressure in a body cavity and produces an output indicative of the sensed pressure; and
    a controller, responsive to said output of said body cavity pressure sensor, controlling said pressure waves to occur at a frequency and duty cycle to sum said pressure waves in a way to cause and control a quantity of said pumping by controlling said pinching mechanism to create a new pressure wave at a time when another wave is reflected to a location of said pinching mechanism,
    wherein said pinching mechanism includes a first actuator part pressing against and capable of at least partially constricting a first portion of said length of tubing, and a second actuator part, pressing against and capable of at least partially constricting a second portion of said length of tubing, spaced from said first portion of said length of tubing, wherein said controller controls said first and second actuator parts to sum said pressure waves, using a pattern of pinching said first actuator part and said second actuator part that sustains a pressure gradient in a way that lowers body cavity pressure, and
    wherein said one of said actuator parts is operable to completely pinch off a first portion of said length of tubing when completely actuated, based on said output.

* * * * *